United States Patent
Chandler et al.

[11] Patent Number: 5,830,180
[45] Date of Patent: Nov. 3, 1998

[54] FLUID MANAGEMENT SYSTEM FOR ARTHROSCOPIC SURGERY

[75] Inventors: W. Jeffrey Chandler, Phoenix; John Kane, Scottsdale, both of Ariz.; Michael J. Egan, Los Altos, Calif.; Howard S. Phillips, Haverhill, Mass.; James S. Roundy, Gilbert; Ernest W. Cassaday, Show Low, both of Ariz.; Roger Etherington, Newport Beach, Calif.

[73] Assignee: Aquarius Medical Corporation, Scottsdale, Ariz.

[21] Appl. No.: 744,883

[22] Filed: Nov. 8, 1996

Related U.S. Application Data

[63] Continuation-in-part of Ser. No. 683,745, Jul. 17, 1996.

[51] Int. Cl.$^6$ .................................................. A61M 31/00
[52] U.S. Cl. ................................. 604/65; 604/35; 604/67
[58] Field of Search ................................. 604/30, 48, 65, 604/67, 259, 35

[56] References Cited

U.S. PATENT DOCUMENTS

| | | |
|---|---|---|
| 3,678,932 | 7/1972 | Hudson .................................... 604/259 |
| 4,127,123 | 11/1978 | Bird . |
| 4,180,074 | 12/1979 | Murry et al. . |
| 4,338,933 | 7/1982 | Bayard et al. . |
| 4,413,988 | 11/1983 | Handt et al. . |
| 4,432,765 | 2/1984 | Oscarsson . |
| 4,436,277 | 3/1984 | Robak et al. . |
| 4,439,193 | 3/1984 | Larkin . |
| 4,461,281 | 7/1984 | Carson . |
| 4,489,750 | 12/1984 | Nehring . |
| 4,561,431 | 12/1985 | Atkinson . |
| 4,585,441 | 4/1986 | Archibald . |
| 4,635,621 | 1/1987 | Atkinson . |
| 4,650,462 | 3/1987 | DeSatnick et al. . |
| 4,679,596 | 7/1987 | Olson . |
| 4,705,464 | 11/1987 | Arimond . |
| 4,705,505 | 11/1987 | Fried . |
| 4,767,289 | 8/1988 | Parrott et al. . |
| 4,820,265 | 4/1989 | DeSatnick et al. . |
| 4,840,621 | 6/1989 | Larkin et al. . |
| 4,842,028 | 6/1989 | Kaufman et al. . |
| 4,902,277 | 2/1990 | Mathies et al. . |
| 4,940,457 | 7/1990 | Olson . |
| 4,964,261 | 10/1990 | Benn . |
| 5,000,733 | 3/1991 | Mathies et al. . |
| 5,037,386 | 8/1991 | Marcus et al. . |
| 5,059,173 | 10/1991 | Sacco . |
| 5,098,377 | 3/1992 | Borsanyi et al. . |
| 5,131,823 | 7/1992 | Guignard . |
| 5,152,746 | 10/1992 | Atkinson et al. . |
| 5,207,642 | 5/1993 | Orkin et al. ............................... 604/65 |
| 5,242,407 | 9/1993 | Struble et al. . |

*Primary Examiner*—Michael Powell Buiz
*Assistant Examiner*—Julian W. Woo
*Attorney, Agent, or Firm*—Majestic, Parsons, Siebert & Hsue

[57] ABSTRACT

An improved fluid management system for irrigation of a body cavity and in particular for use in arthroscopic surgery having a pressurized fluid circuit for supplying irrigation fluid and a vacuum fluid circuit for withdrawing waste fluid from the cavity. In a preferred embodiment there is an uninterrupted fluid supply comprised of a plurality of sterile solution saline bags with an automatic spiker to perforate the bags. The system is processor controlled with numerous safety and design features to automate arthroscopy to the highest degree possible. Some of the features include the monitoring and tracking of cavity pressure and flow rates to predetermined pressure and flow rates, tracking cavity to mean blood pressure, overpressure protection, a plurality of pressure and flow rate baseline settings, monitoring, setting and controlling saline supply, and specialized functions for providing pressure and flow rates for typical surgical procedures such as lavage, clear view, and burr/shaver. One or more vacuum discharge lines may be provided with an automatic self-cleaning feature. The system is compact and optionally employs a number of disposable components, including a novel fluid accumulator. In one preferred embodiment there is a compact gravity irrigation fluid management apparatus employing automatic pressure regulating means. An improved console for monitoring out-of-fluid anomalous conditions is also disclosed.

8 Claims, 16 Drawing Sheets

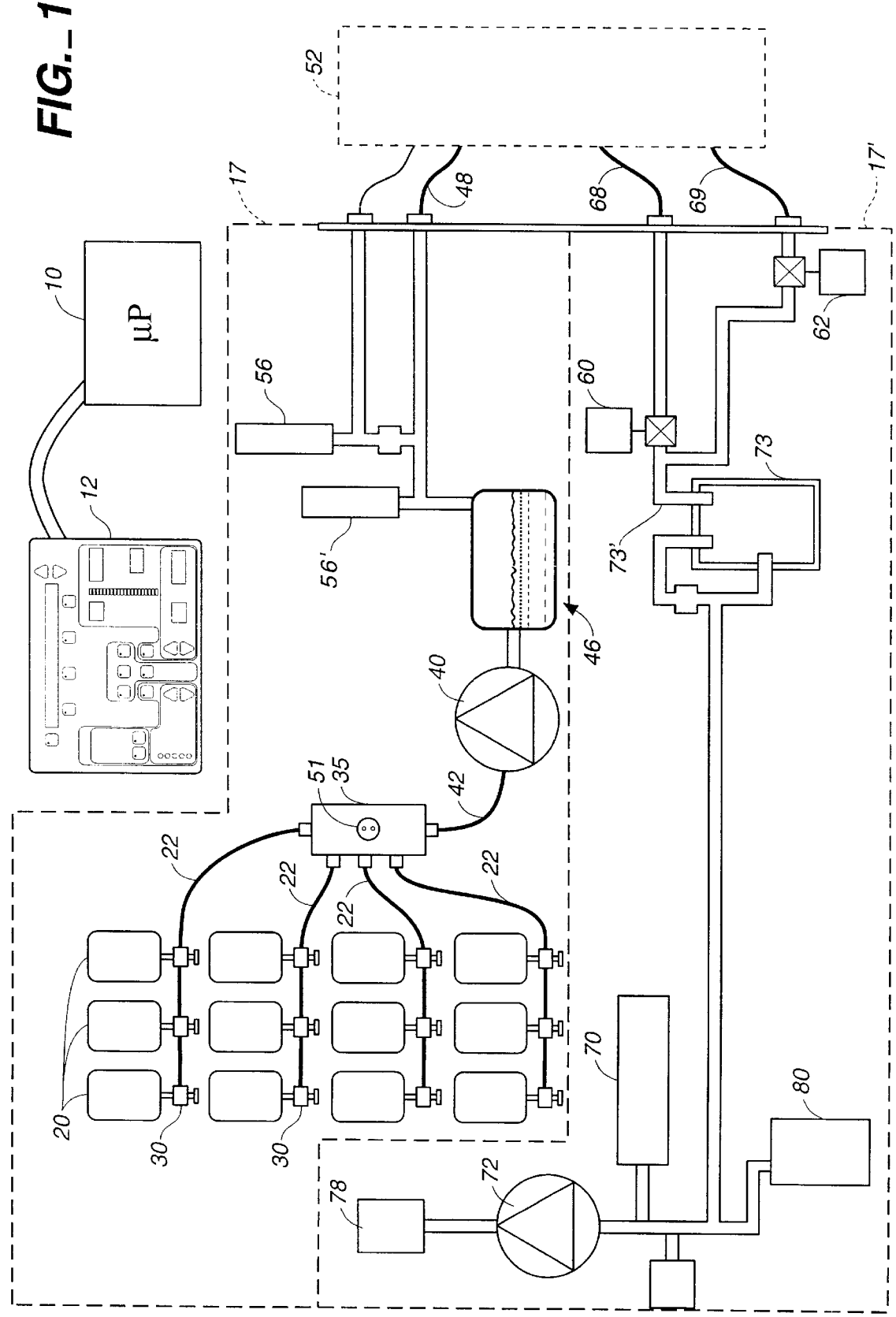
FIG._1

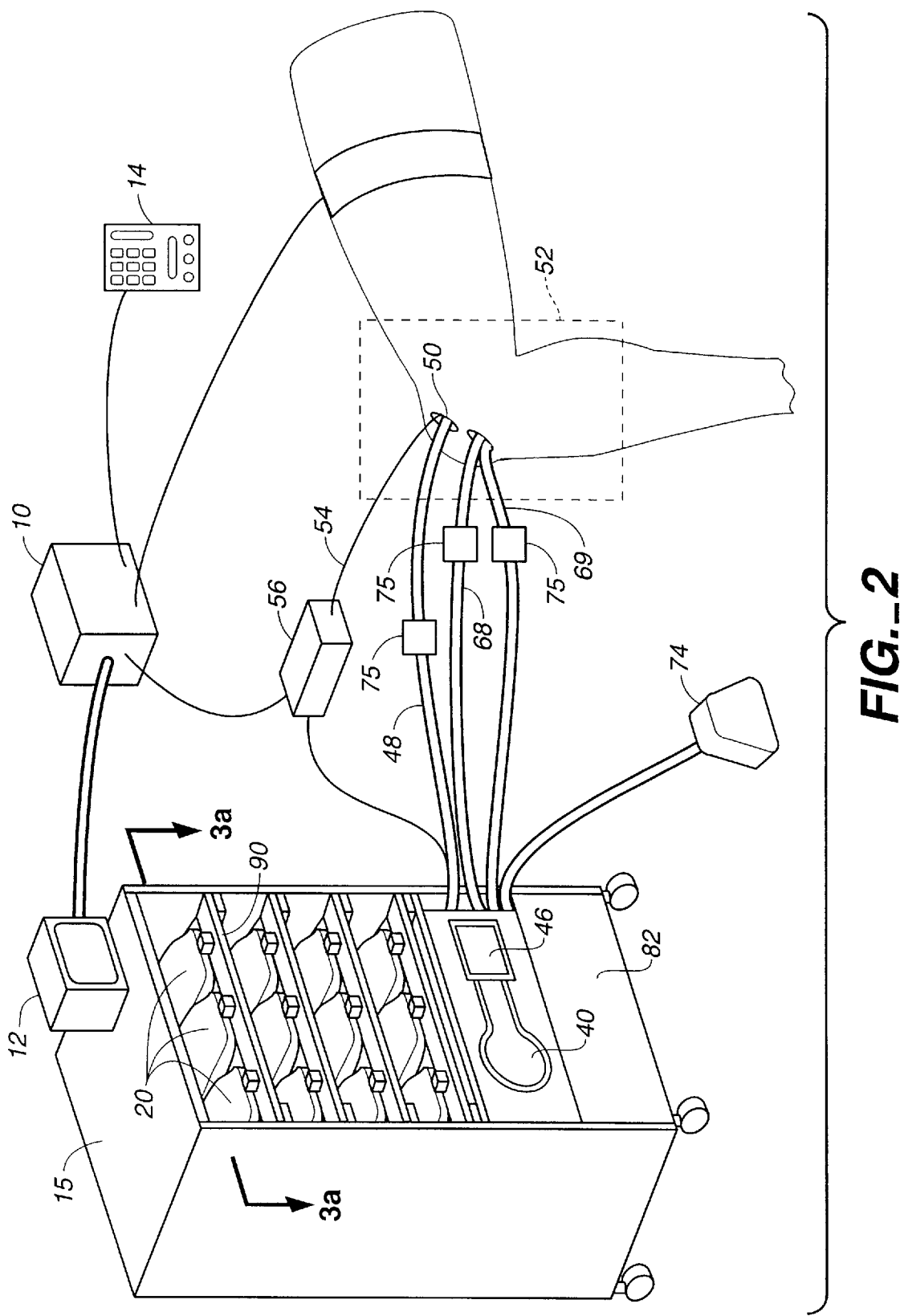
FIG._2

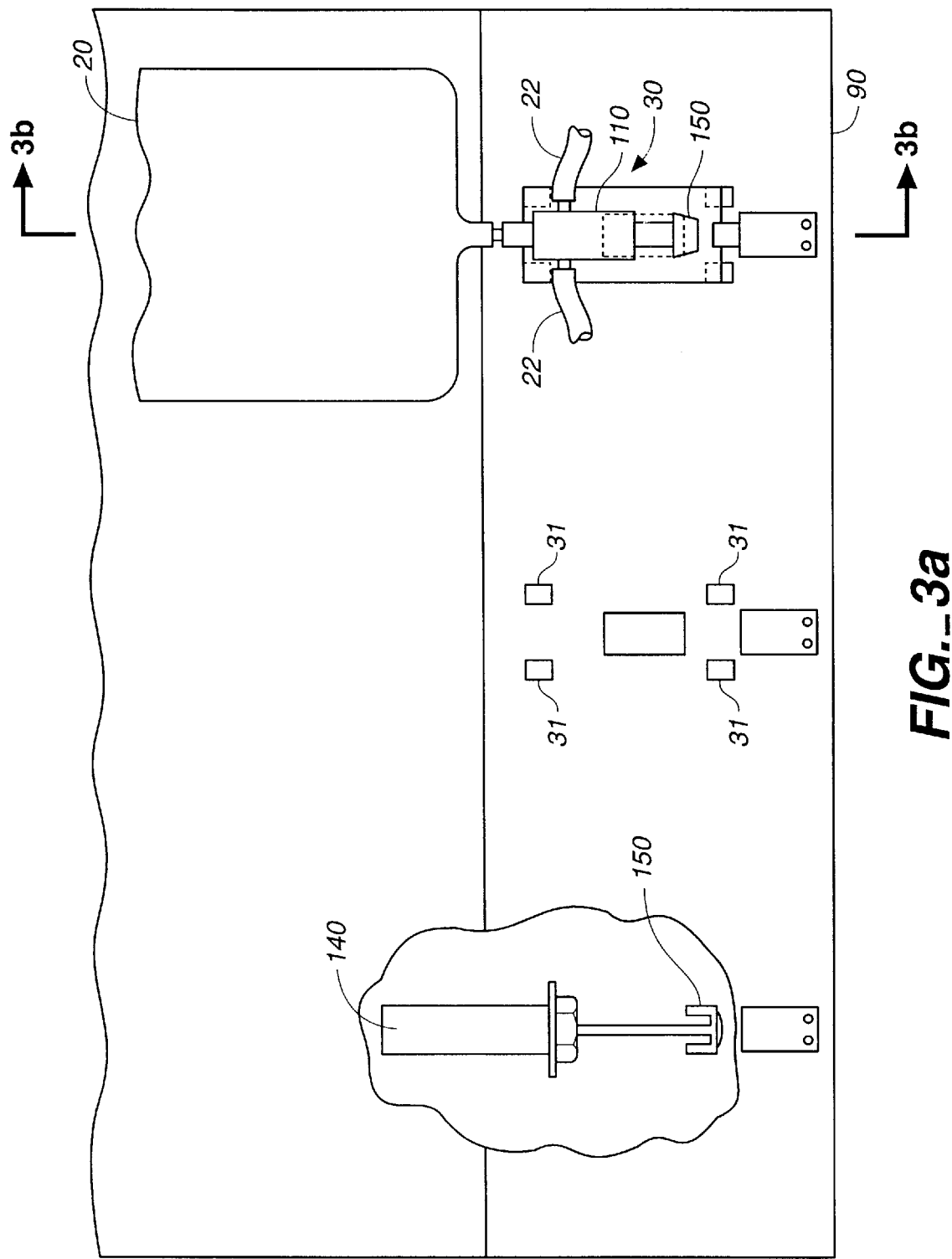
FIG._3a

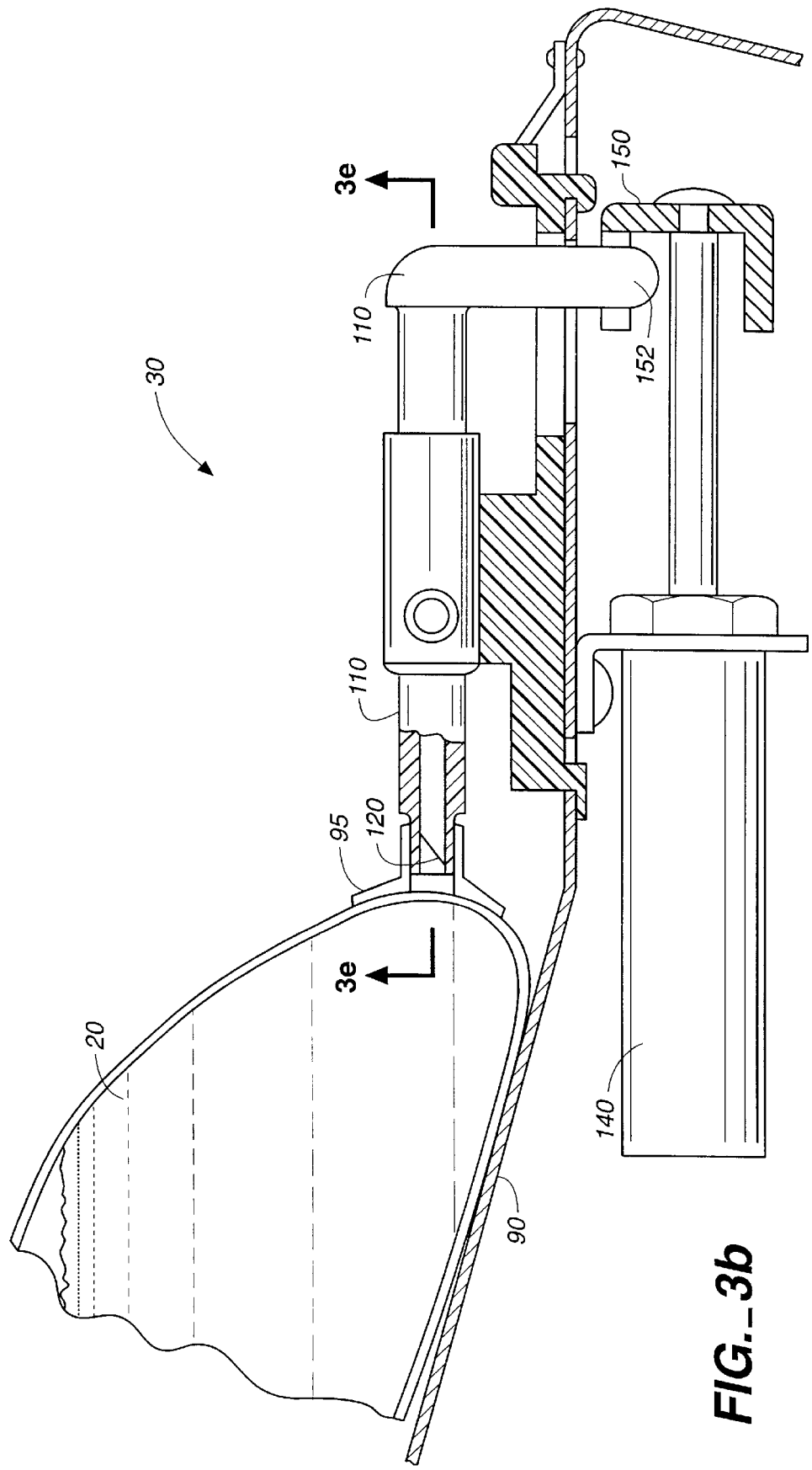

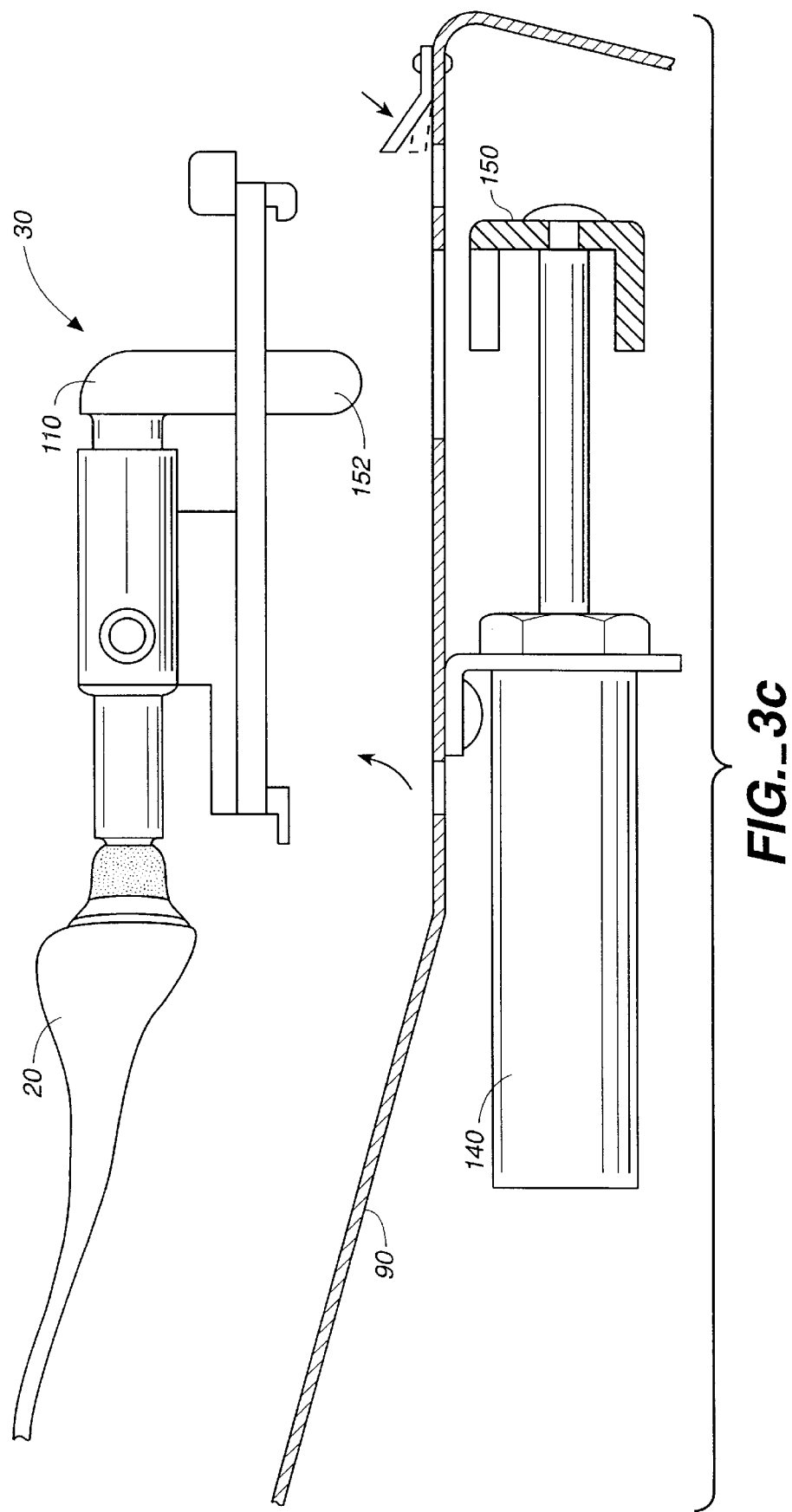
FIG._3c

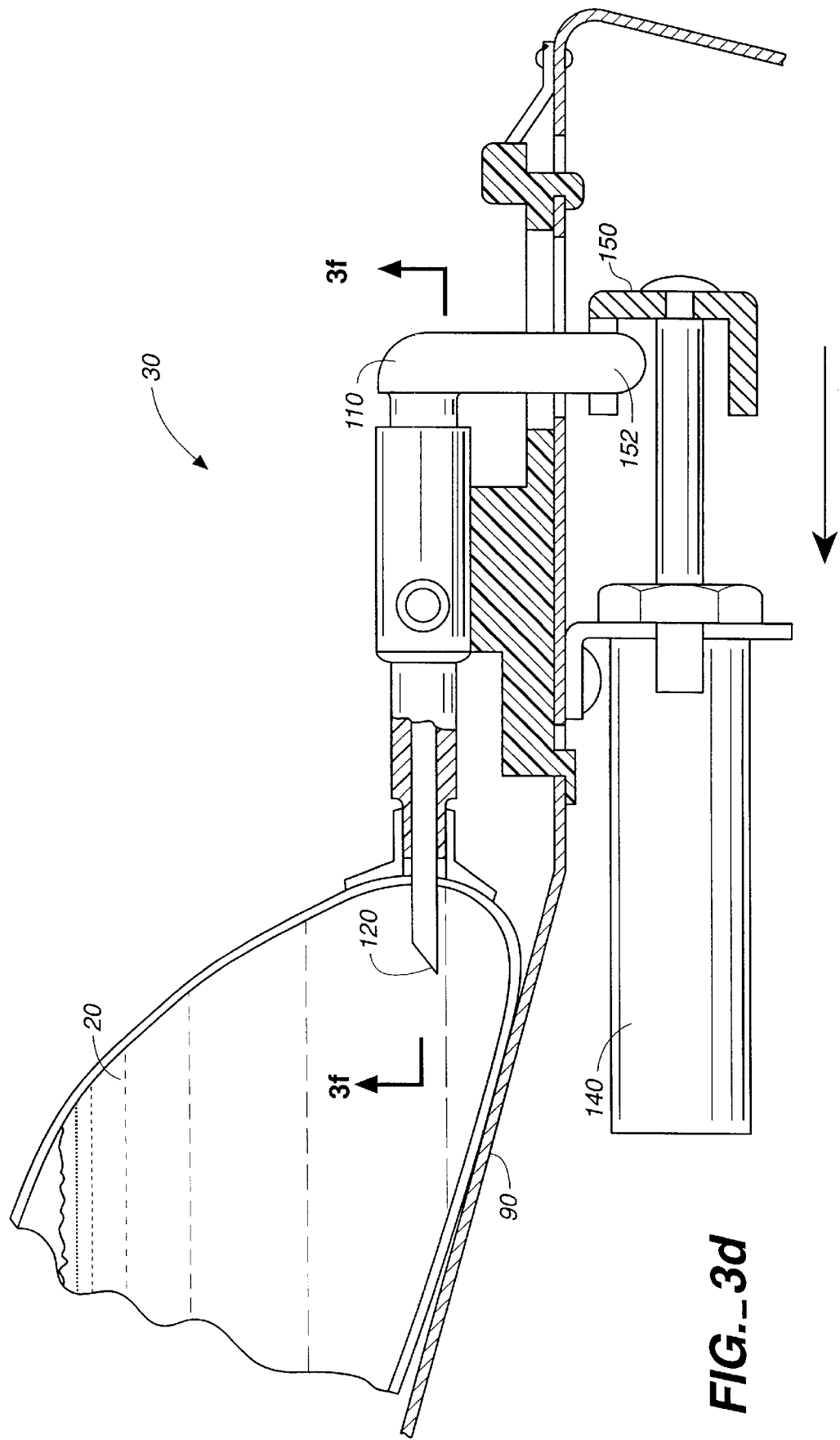

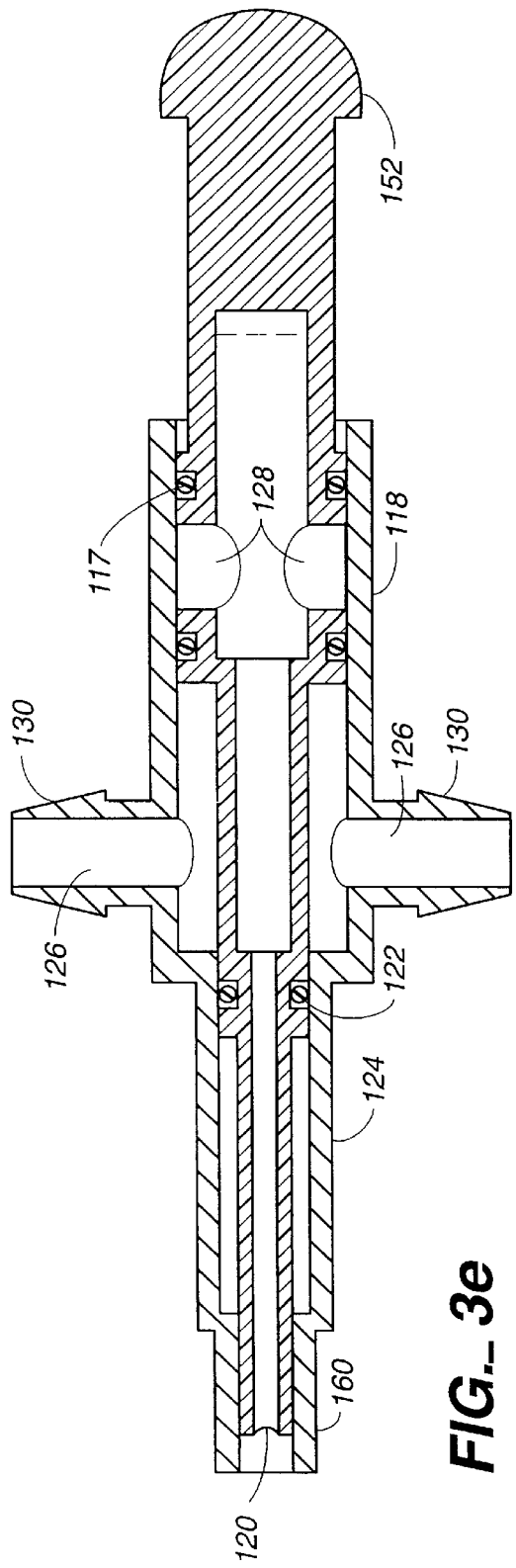
FIG._3e
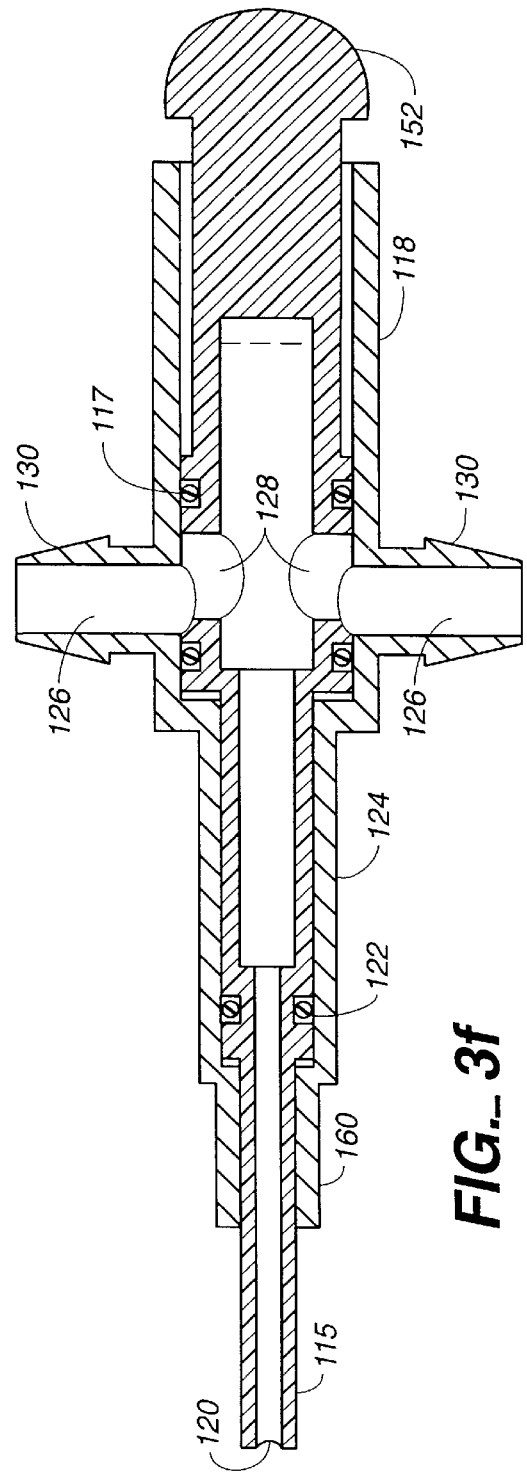
FIG._3f

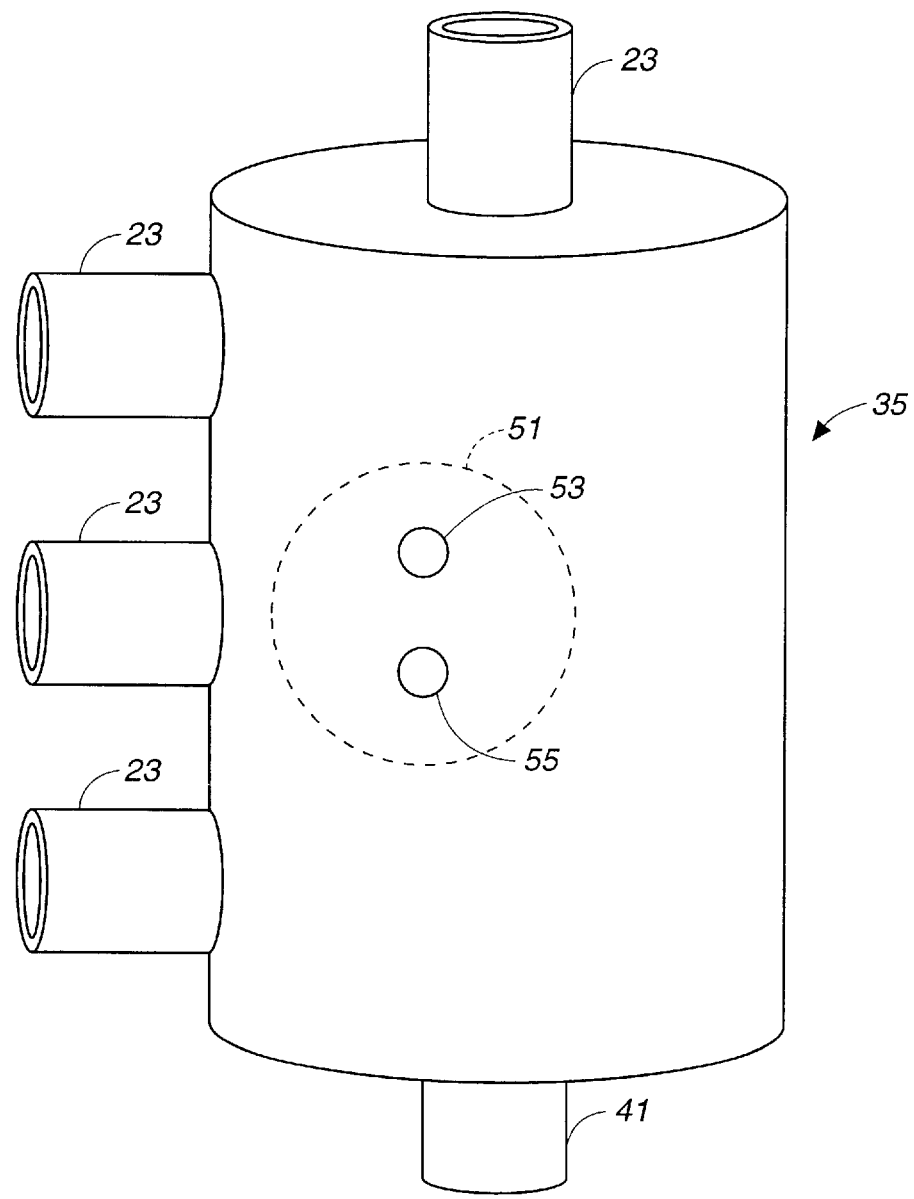
FIG._4

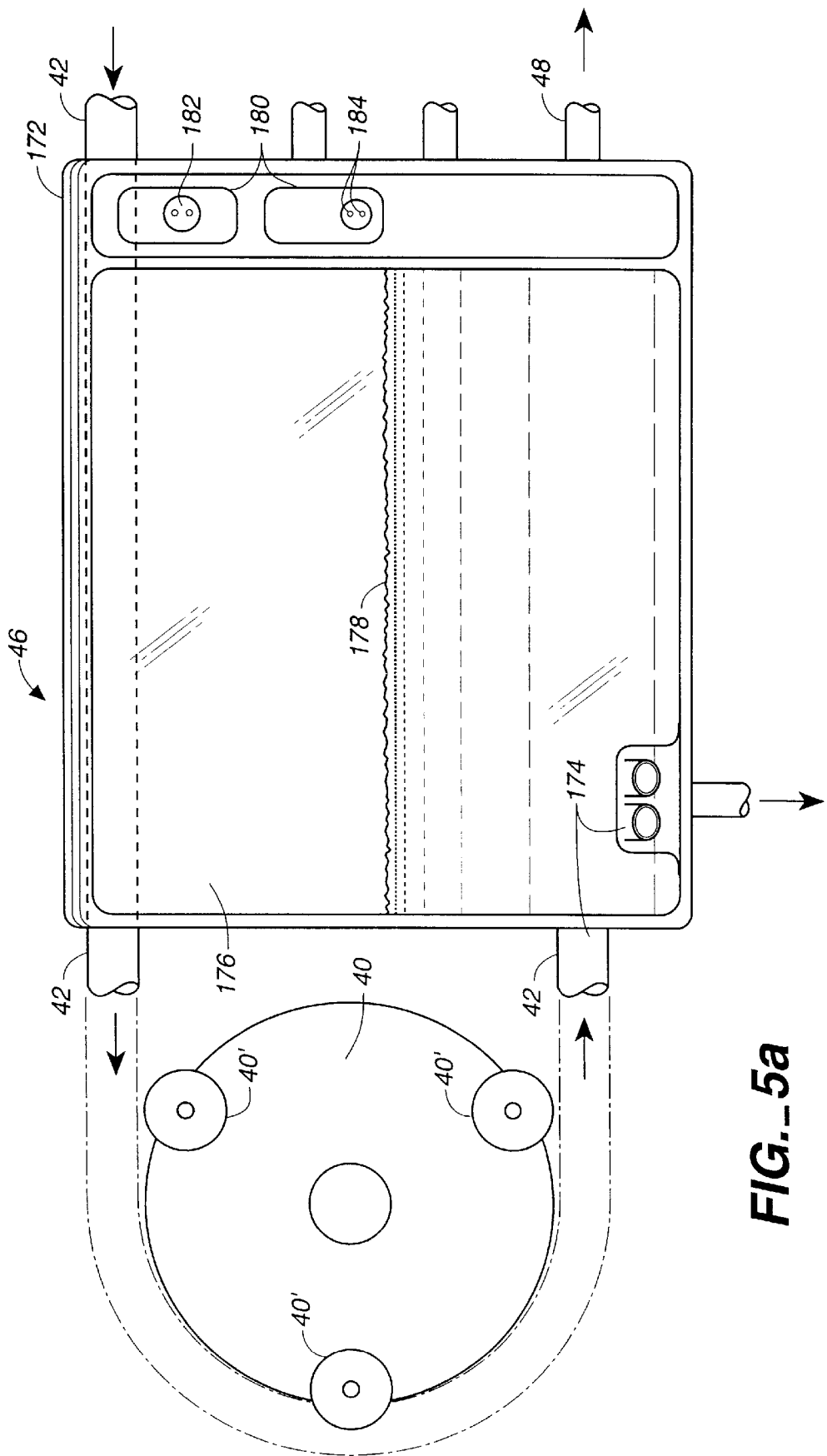
FIG._5a

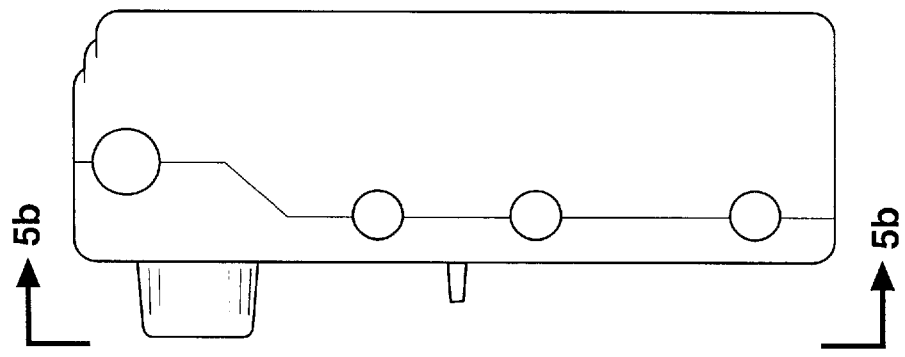
FIG._5c
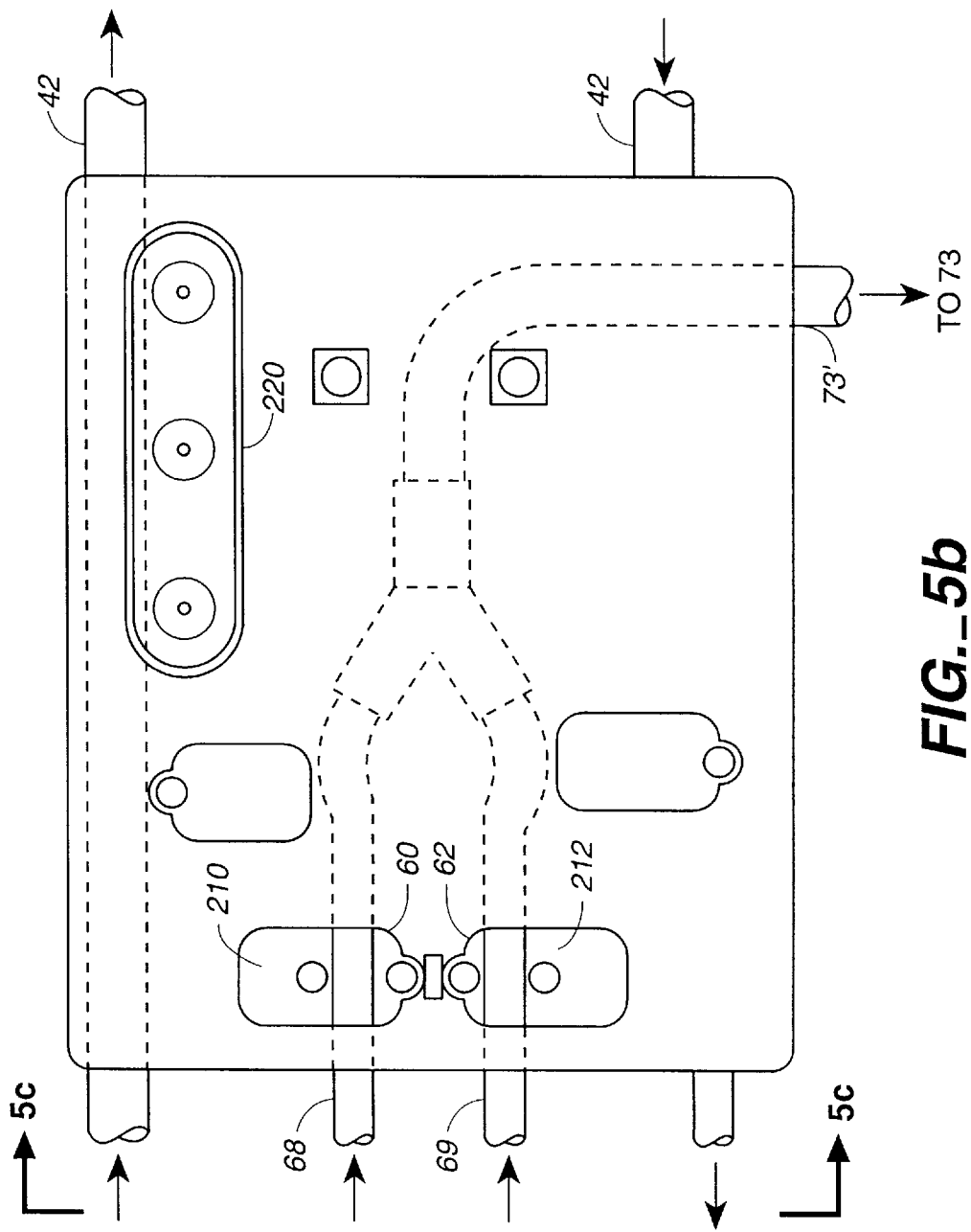
FIG._5b

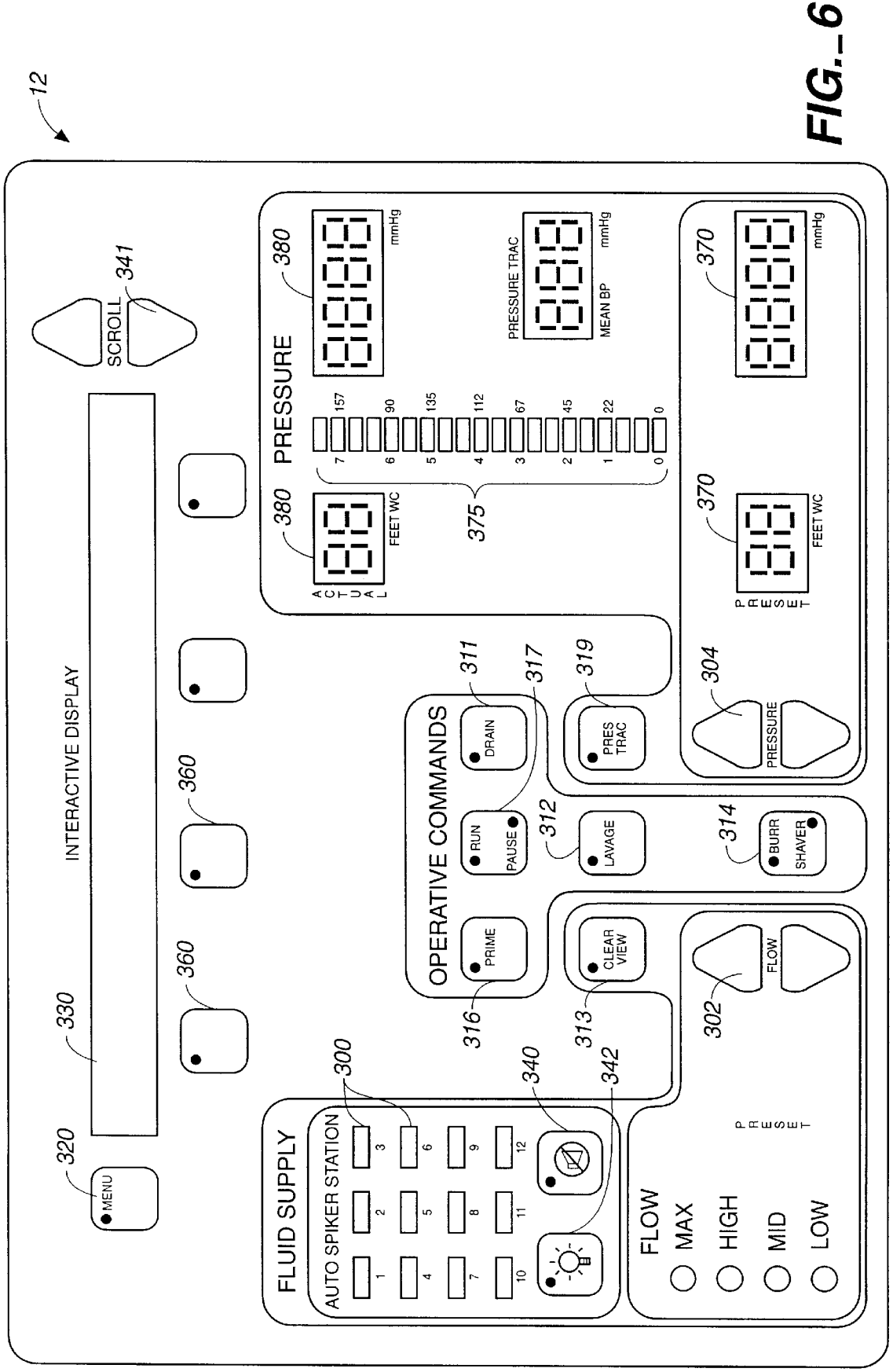
FIG._6

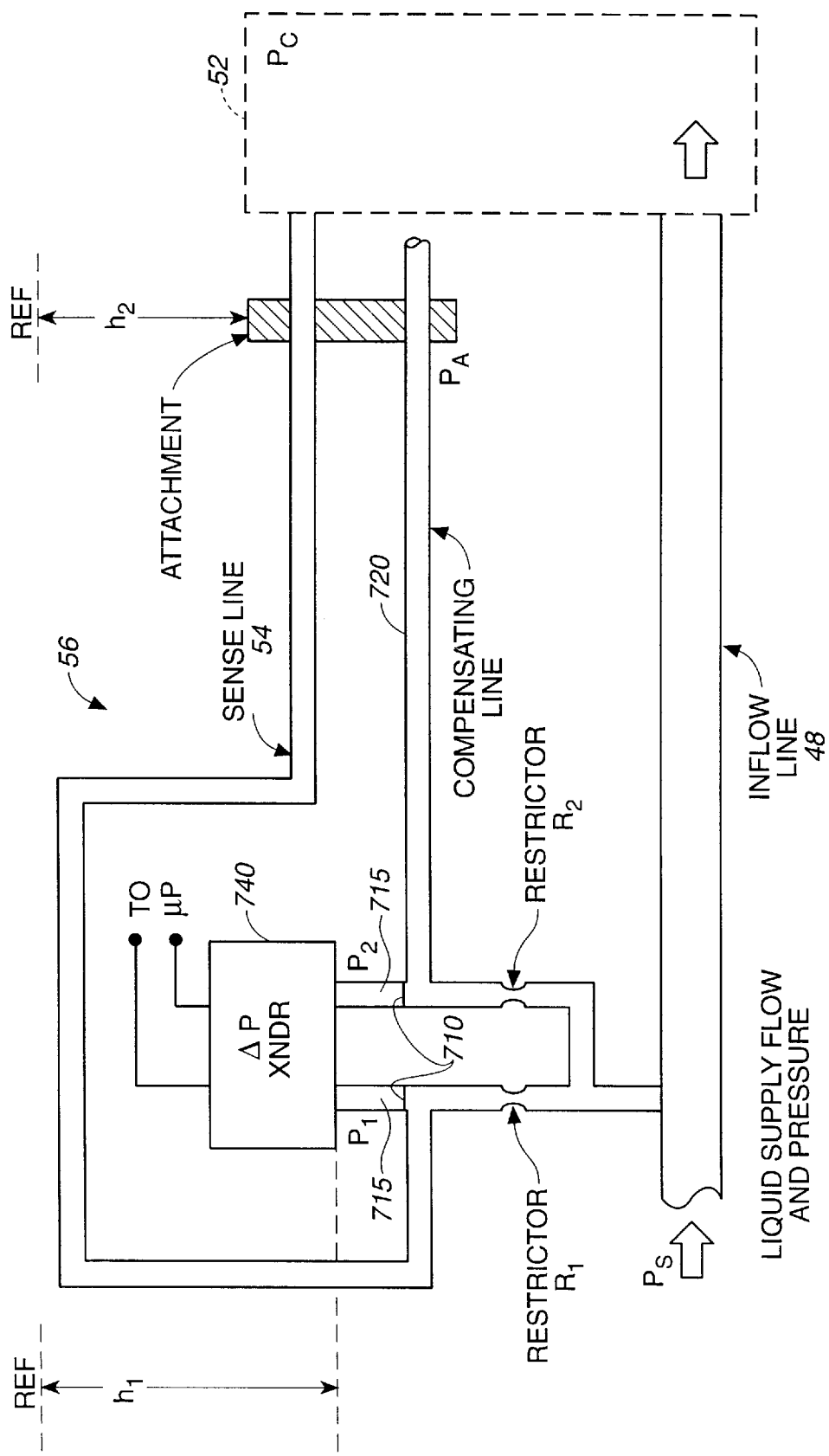
FIG._7

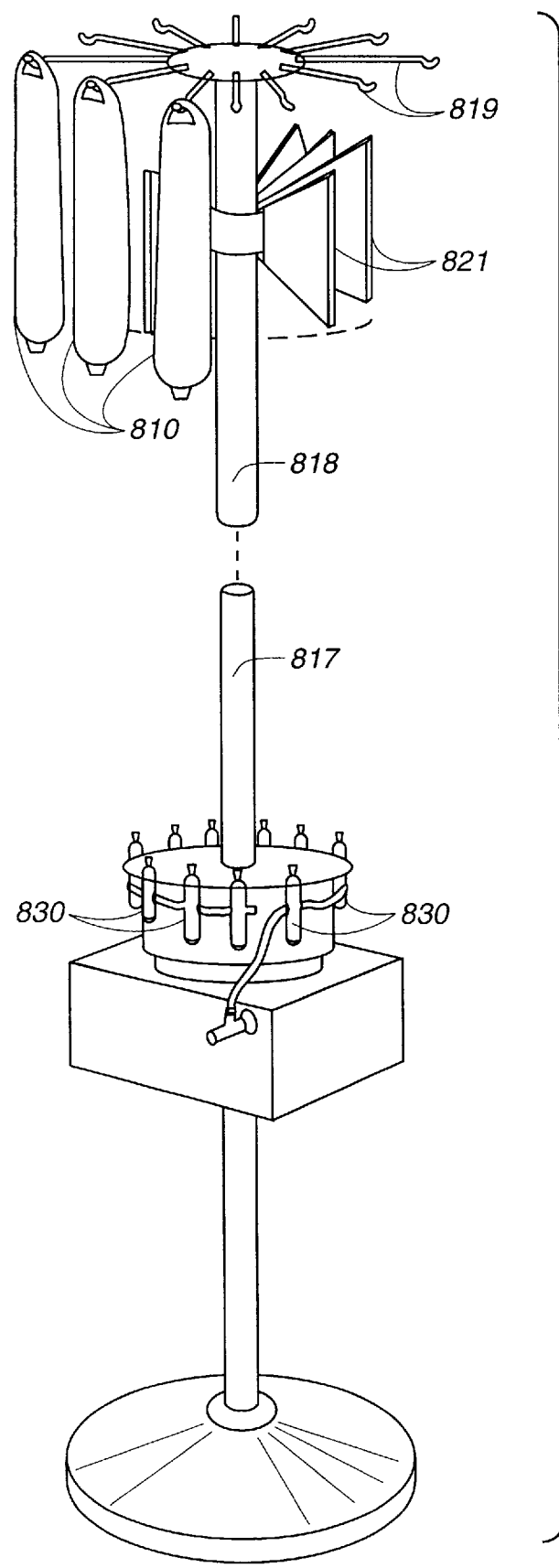
FIG._8

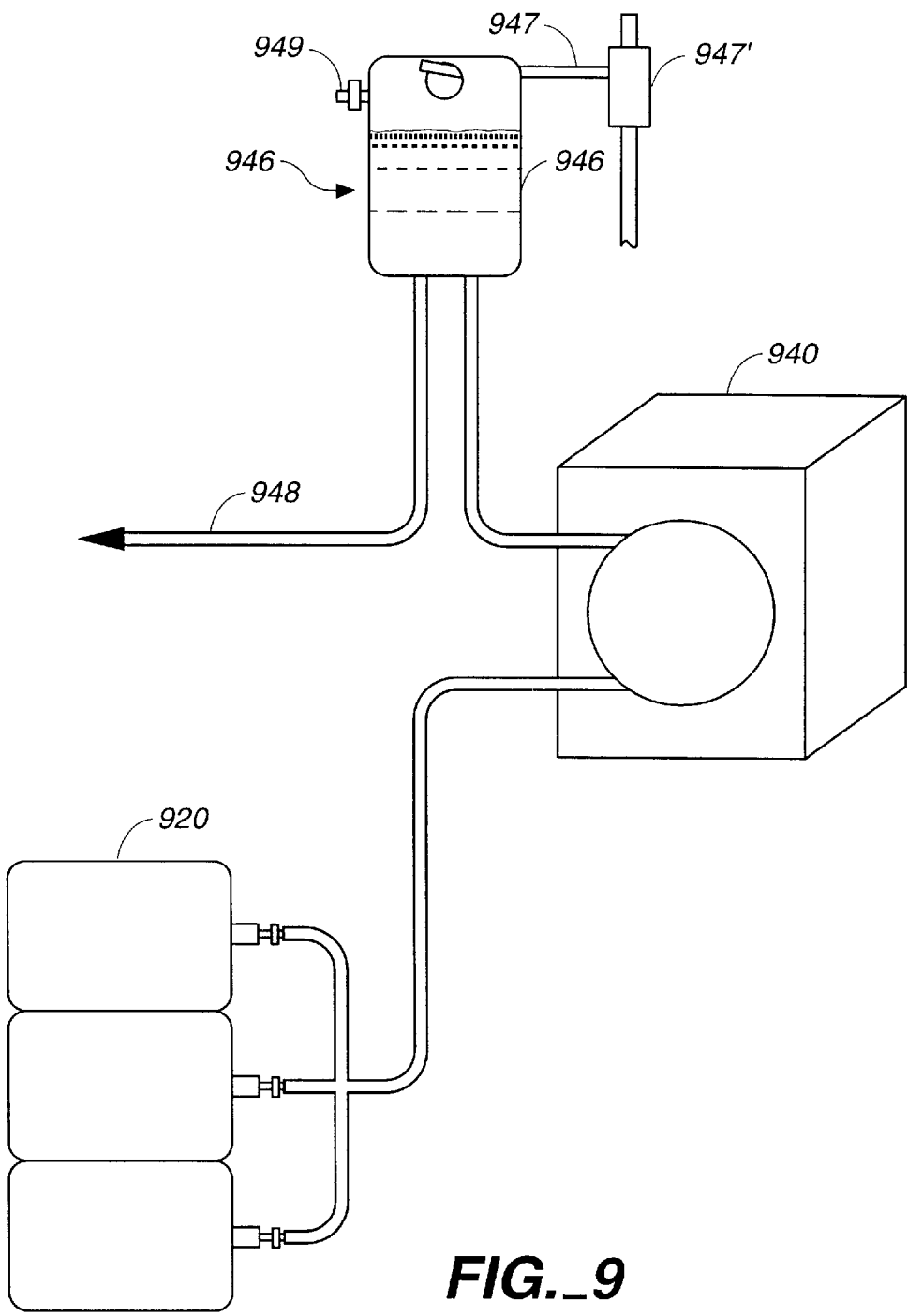
FIG._9

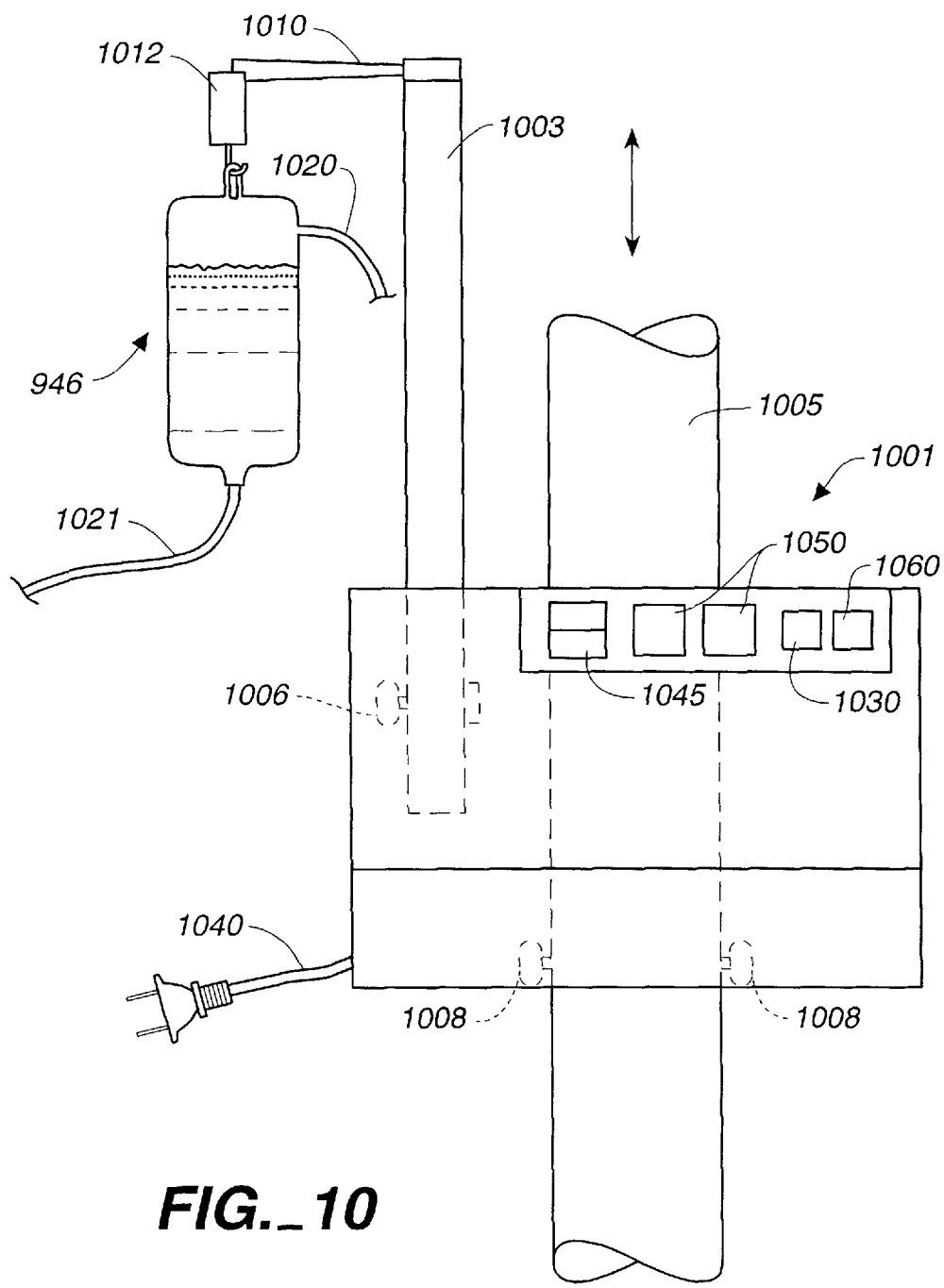
FIG._10

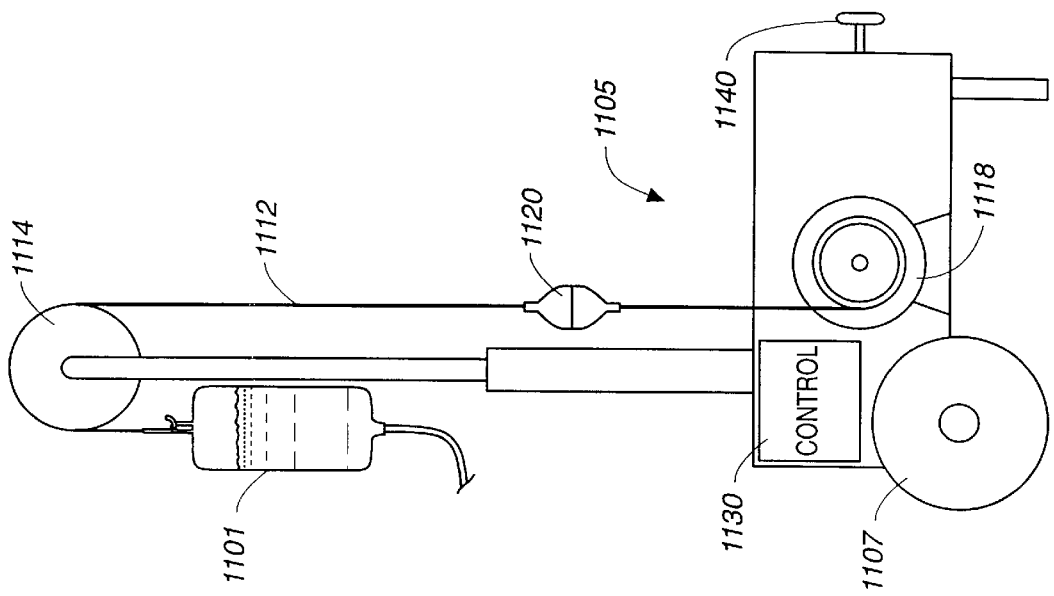
FIG._11B
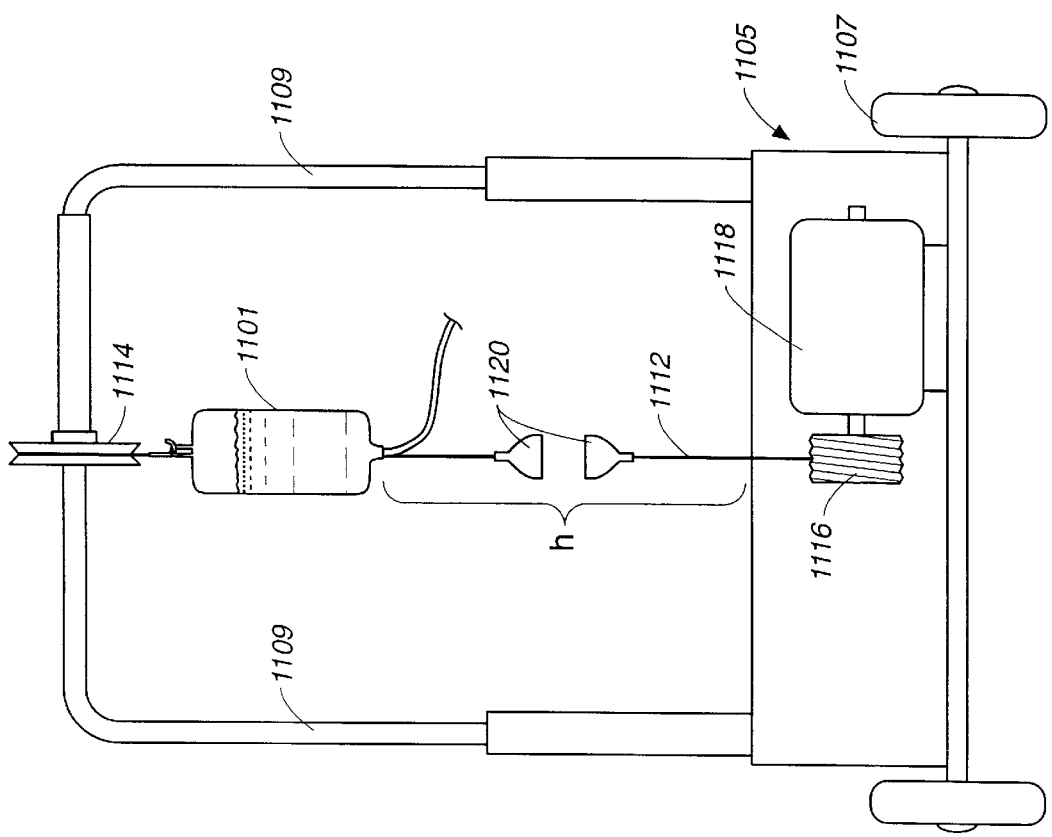
FIG._11A

FLUID MANAGEMENT SYSTEM FOR ARTHROSCOPIC SURGERY

CROSS-REFERENCE TO RELATED APPLICATION

This application is a continuation-in-part application based on patent application Ser. No. 08/683,745, filed Jul. 17, 1996.

FIELD OF THE INVENTION

The present invention generally relates to endoscopic procedures which require a fluid medium, and more particularly with arthroscopic surgery.

BACKGROUND OF THE INVENTION

Arthroscopic surgery is a minimally invasive therapeutic and/or diagnostic procedure, during which small sized visualization and surgical tools are introduced into a joint body cavity (most commonly a knee) through very small incisions. Typically, at least three incisions are employed for a therapeutic procedure and at least two for a diagnostic procedure. During the surgery, irrigation of the joint is necessary for the following reasons:

(1) Distention of the joint is desirable for better visualization and access achieved by an increased joint or tissue separation. This is accomplished by application of pressure through the medium of the irrigation fluid to the tissue structure and causes closing of the blood vessels;

(2) Flow of the irrigation fluid through the joint keeps the field of view clear and often evacuates most of the loose debris;

(3) The fluid keeps the joint lubricated and replaces lost body fluids.

There are thus two independent factors at work here, the pressure and the flow rate of the irrigation fluid. The function and need for independent control of these two factors can be illustrated by the following situations:

(a) There are times during the surgical procedure when one needs to view and reach the far or posterior end of the joint. The joint separation needs to be increased without any need for an increased flow. A higher pressure in the joint will achieve this.

(b) If there is debris or bleeding in the joint, a quick flush of fluid is needed to clear the field of view. Such conditions require a higher fluid flow rate and with slightly higher pressure, assuming the joint separation is adequate.

(c) When an accessory instrument is used, like a shaver with wall suction, a higher fluid inflow is required to keep up with the increased demand and prevent the joint from collapsing. A higher flow rate but the same set pressure is needed here. Traditionally, the typical solution is to use sterile fluid bags hung above the level of the patient which are connected to the joint by a tube. The bags are raised to obtain more pressure and the flow rate is controlled by using variable clamps on the tubing leading to and away from the patient. The control for the two operations is manual and decided upon by the surgeon.

Furthermore, when burring and shaving large amounts of debris forms and can quickly block the exit port leading from the body cavity.

Thus there is a continuing need to improve automated pressure regulating systems and other systems used in arthroscopic or other fluid related procedures in order to provide for automated handling of various aspects of the procedure which the surgeon or supporting staff would otherwise need to handle manually.

There is further a need during arthroscopic surgery—which can last from a few minutes to several hours—to change saline bags. Up to a dozen or more saline bags may be required in an operation, and during a manual spiking of the bag, when infusing saline solution from the bag to the body cavity being operated on, air may be accidentally introduced into the fluid tube leading to the body cavity and may interfere with visualization, and saline solution may be spilled. Saline bags may also run dry unless medical personnel attend to the bags. In addition, often the number of bags needed to complete the operation is not estimated properly. Furthermore, in gravity fed pressurized saline infusions of the type described above, the pressure inside the tube leading to the body cavity can only be varied by raising or lowering the saline bag, which limits the range of pressure achievable and is not accurate.

BACKGROUND INFORMATION

U.S. Pat. No. 4,650,462 (the "462 patent" to DeSatnick et al.) discloses an irrigation system for use in arthroscopic surgery that employs pressure feedback to control pressure and flow rates. However, the suction in the '462 patent is due solely to atmosphere from a syphon effect, and there is no provision for providing a greater than atmosphere vacuum. Furthermore, the '462 patent does not supply pressurized fluid in the inflow line greater than the gravity head from the supply of saline solution, that is, the pressurized supply fluid is limited by the height of the saline bag rack, which is in turn is limited by the height of an average nurse and the ceiling height of the operating theater. In addition, the pressure feedback control system of the '462 patent, though a closed loop, tends to react passively to changes in body cavity pressure, to vary the outflow valve closing rate and the speed of the inflow line pump, in a lagging manner, with no ability to actively predict changes in pressure and/or flow rate. Rather, the control system hunts and seeks to find the optimal flow rate and pressures in a passive, mechanical manner once an imbalance in joint cavity pressure is detected. As a consequence, the system described in the '462 patent seems to be prone to relatively wide swings in actual flowrate and pressure about the desired parameters that is disconcerting to surgeons. Furthermore, there is no provision in the '462 patent for the automatic, uninterrupted supply of saline solution throughout an operation.

The present invention offers an improved design to the irrigation device found in the '462 patent by incorporating, among other features, a high vacuum (greater than from atmosphere alone) suction from the body cavity being irrigated, improved operation of the flow control using a plurality of valves downstream of the body cavity, a more accurate pressure transducer, a pressurized inflow line that does not depend solely on the gravity head, a spiking mechanism for saline bags for the continuous flow of fluid from the saline bags with a plurality of built-in safety features, and a microprocessor controlled feedback operation that is not passive but, using software, can actively predict and anticipate changes in flowrate and/or pressure to achieve smoother tracking of pressure and flow rates.

In conventional arthroscopic or fluid dependent systems, pressure is sensed in the surgical cavity with either a relatively large diameter dedicated cannula or is incorporated into an inflow or outflow cannula. Liquid/air separation is accomplished with a diaphragm immediately adjacent to the operating site. Some disadvantages of such conventional cavity pressure sensing systems are that: a) the pressure sense line and liquid/air chamber adds bulk to the irrigation fluid supply line and are cumbersome to handle; and b) the elastic forces from the liquid/air diaphragm either introduce errors in pressure readings or system has to be calibrated to obtain accurate pressure data. The pressure sensing system of the present invention is an improvement over this prior art.

SUMMARY OF THE INVENTION

The invention, which in one preferred embodiment is called the AC2000 Fluid Management System or Aqua-Center 2000 (AC2000), is a complete, self-contained, portable fluid management system for use in arthroscopic surgical procedures or any other fluid dependent surgical irrigation procedure. The major features of the portable, self-contained fluid management system include a self-contained and automatic fluid supply system comprising a sterile solution supply cabinet that allows for an adequate supply of sterile solution bags for completing most arthroscopic or other fluid related procedures in an automated manner; an automatic fluid delivery and control system including a pump and inflow tubing connected to a cannula or scope; an automatic fluid retrieval system including tubing from an outflow cannula or scope and a cavity pressure control valve, and including tubing from a motorized shaver or other vacuum related instruments with a liquid sensor and control valve for providing for the flow requirements of a motorized shaver or other vacuum related instruments; a cavity pressure sensing and control system which maintains cavity pressure at a desired level; a disposable tubing system comprising an inflow line, pressure sense line, pressure compensation line, patient outflow line, motorized shaver outflow line, floor waste retrieval line, and drape fluid retrieval line; a self-contained waste collection system including a waste receiver cart with capacity for an adequate quantity of waste receiver canisters to complete most arthroscopic or other fluid related procedures, and a vacuum system, driven independently of the fluid drive pump, for driving the fluid retrieval system and floor and drape vacuum pickup.

More specifically, the present invention includes the following features:

1. Automatically sequencing and spiking of sterile solution bags as needed to provide an uninterrupted supply of fluid throughout the case.
2. Means for sensing of pressure in the surgical cavity.
3. Means for setting desired cavity pressure manually or automatically in relationship to the patient's blood pressure.
4. Ability to set flow and pressure independently of each other.
5. Controller for maintaining set cavity pressure.
6. Out of Tolerance Flow Controller for adjusting from set flow rate when required to maintain set cavity pressure.
7. A liquid sensor and controller to automatically provide for the flow needs of most any motorized shaver and/or other vacuum related instruments.
8. Auto-sequenced and manual functions displayed on a console including lavage, clear view, prime, drain, burr, pause/run, alarm silence, power on/off, and a surgical diagnostic mode which provides means for setting pressure for distention of surgical cavity with no egress cannula.
9. A help mode (message center) on a console to help users set up or to identify malfunctions.

Accordingly, it is one object of the present invention to provide an automated fluid delivery system for the continuous supply of fluid to a body cavity from a plurality of sterile bags (or containers), with the minimum amount of human intervention, and without having to interrupt an operation to change bags. The present invention further employs safety features to indicate when flow is cut off, when flow is resumed, and sensors and check valves for overpressure, for pressure sensing within the body cavity, and for suction backflow.

Thus in one preferred embodiment of the present invention for use in arthroscopy, there is provided in an apparatus (the AquaCenter 2000, AC2000) for storing saline bags and providing total fluid management in arthroscopy. The apparatus has a user-input console, and a door opening to a series of elevated and inclined racks. Each rack holds up to three saline bags, chained together in series. All the bags lead to an inflow manifold where a safety device (a flow-interrupt/air sensor valve) is present. From the manifold a positive displacement peristaltic pump pumps the saline fluid to a removable cartridge accumulator, where bubbles are removed and surges are attenuated. Thereupon, in response to an improved pressure transducer sensing pressure inside the body cavity, to user input as to the type of operation being performed and from software, a processor controls pump speed and/or one or more exit valves to vary the degree of pressure and/or flow rate inside the body cavity being irrigated. Downstream of the body cavity, and working independently from the compressor driving the positive displacement pump, is a vacuum compressor that keeps a vacuum tank at high vacuum (potentially much greater than atmosphere) which can be used both with particular surgical tools and in connection with an exit tube leading from the body cavity to suck waste fluid and debris from the body cavity. A waste trap is employed to filter out solid waste from the waste fluid slurry.

In another aspect of the present invention, there is provided an improved pneumatically driven linear actuator spiking assembly employing a spiker needle/trocar to drive a normally withdrawn saline infusion bag spike into the saline bag. An arming switch on the apparatus acts as a safety.

In yet another aspect of the present invention there is disclosed an improved pressure transducer that employs a novel design to make pressure readings inside a body cavity more accurate.

In a further aspect of the present invention there is provided an automatic body cavity pressure tracking feature that automatically varies cavity pressure according to the patient s mean blood pressure.

BRIEF DESCRIPTION OF THE DRAWINGS:

FIG. 1 is a schematic of the operation of the principal components used in the present invention.

FIG. 2 is a perspective view of one preferred embodiment of the cabinet housing assembly of the present invention.

FIG. 3 shows one preferred embodiment of the spiker assembly of the present invention:

FIG. 3a shows a top plan view of the saline bag spiker assembly;

FIG. 3b shows a side cross sectional view;

FIG. 3c and 3d show the spiker perforating a saline bag; and

FIGS. 3e and 3f show top cross-sectional views of the piston and piston housing of the spiker assembly.

FIG. 4 shows a perspective view of the flow interrupt sensor manifold of the present invention.

FIGS. 5a–c show one preferred embodiment of the removable accumulator cartridge of the present invention:

FIG. 5a shows the front of the accumulator;

FIG. 5b shows the back view of the accumulator; and

FIG. 5c shows the side view of the accumulator.

FIG. 6 is a front view of the console used in a preferred embodiment of the present invention.

FIG. 7 is a schematic of the improved cavity pressure sensing system of the present invention.

FIG. 8 is a perspective view of another embodiment of the present invention.

FIG. 9 is a schematic of another embodiment of the present invention.

FIG. 10 is a schematic of a device to be used with the embodiment of the present invention as depicted in the configuration of FIG. 9.

FIGS. 11A and 11B depict another embodiment of the present invention, having an automatic pressurizing means employing a gravity feed.

DETAILED OF THE PREFERRED EMBODIMENTS

Turning attention to FIGS. 1 and 2 there is shown the overall configuration of the apparatus of the fluid management system, which in a preferred embodiment is termed the AquaCenter 2000 (AC2000). It should be understood by one skilled in the art that while in the preferred embodiment the supply of irrigation fluid is a sterile fluid such as saline solution, the present invention may be used to supply an uninterrupted supply of any body fluid to a body cavity, including the supply of blood, blood plasma or medicated fluids.

The AC2000 fluid management apparatus is processor controlled, by processor 10, with user input from console 12 and/or a hand held remote control 14. The AC2000 has a housing 15, which contains a cabinet for storage of sterile solution supply, shown as a plurality of saline bags 20. The fluid management system is shown in FIG. 1 as having a pressurized fluid supply circuit 17 and vacuum assisted waste discharge fluid circuit 17. The AC2000 compactly houses both the pressurized conduit fluid circuit and vacuum conduit fluid circuit, which are separate fluid circuits as indicated by dashed lines 17 and 17' in FIG. 1, in a compact manner side by side in housing 15. Thus in a preferred embodiment of the AC2000 both the vacuum system and the pressurized supply system are compactly housed in the same housing 15, as indicated by FIG. 2, with the supply fluid and discharge conduits spaced compactly together.

In FIG. 2 each shelf of the housing 15 contains up to three bags connected serially to one another through their automatic spiker assemblies, but a fewer or greater number of bags or containers and corresponding spikers may be used. The bags are kept sealed in a sterile condition until needed, and connected to cabinet shelf supply conduits 22 at each rack level, which link together the spiker assemblies, which form a auto-spiker tubing set assembly. The saline bags are spiked with a saline bag spiker assembly allowing fluid to flow along the cabinet supply conduits 22 to a manifold 35 in an uninterrupted manner, without the necessity of changing bags during an operation. The manifold 35 is plugged into a flow interrupt safety switch 51, as described herein. The conduits 22 of the supply cabinet are pressurized, typically at some pressure value greater than atmosphere, and are closed to atmosphere (though safety vents may in incorporated into the conduits in the event of overpressure). From the manifold 35 fluid is driven by and through the pressurized fluid supply pump 40, which may be any kind of pump but preferably a positive displacement pump of the peristaltic kind to avoid fluid contamination by the pump. The saline supply fluid is pumped by a plurality of rollers of peristaltic pump 40 (as shown in FIG. 5a as rollers 40'), working on the flexible tubing against a roller guide track (not shown), which slides open to allow one to withdraw the flexible tubing 42, which leads to and wraps around the peristaltic pump rollers, and is optionally preferably disposable. Saline fluid is driven from the inlet of the peristaltic pump assembly into the inlet of a removable cartridge accumulator 46, which is removable and preferably disposable. Also optionally disposable but reusable upon sterilization is the flexible tubing connected to the cartridge accumulator leading to the patient (supply conduit 48), as well as the discharge tubing (waste fluid return conduits 68, 69) leading from the patient.

Cartridge accumulator 46 serves a variety of purposes, such as allowing any air bubbles trapped in the fluid supply conduits to escape from the saline fluid solution, acting as a surge suppressor, and acting as a pressurized reservoir for the irrigation fluid. The accumulator is closed to atmosphere but has a plurality of escape valves on its back side that vent to atmosphere, as the accumulator can be pressurized at pressures greater than atmosphere to deliver saline solution at pressures greater than conventional gravitational head.

Pressurized irrigation fluid traveling downstream of the cartridge accumulator 46 travels through the patient inflow supply line 48, through a trocar, cannula, Luer fitting, surgical tool or other suitable device attached to the supply line at the incision site 50, and into body cavity 52 (indicated as by dashed lines in FIGS. 1 and 2). A pressure transducer sense line 54 is parallel and in communication with the irrigation fluid supply line 48 and the pressure inside body cavity 52, as described more fully below, and together with the pressure sensing system 56, allows the processor that controls the overall system to make accurate readings of the static pressure inside the knee with respect to atmosphere and the pressure in the fluid supply line 48. Another pressure transducer 56 may sense the pressure inside the supply line 48 and signal the processor. Thereon, based on the sensed pressure data and in response to user input the processor may change the speed of the drive pump 40 and/or the flow rate through the exit valves 60, 62 downstream of the body cavity 52 that control the flow through the discharge conduits 68, 69, to alter the rate of flow into and passing through the body cavity and/or the pressure inside the knee. The software in processor 10 is designed to track preselected desired pressure and flowrates in response to measured and derived pressures and flowrates in an automatic manner.

Downstream of the body cavity 52 are two exit valves, 60 and 62, each controlling the flow through vacuum assisted waste fluid return conduits 68, 69, respectively. The waste fluid return conduits 68, 69 are each connected to body cavity outflow cannula ports at incision sites at the body cavity 52. The valves and waste fluid discharge conduits are part of a hard vacuum fluid discharge system connected to a vacuum tank 70 and serviced by a vacuum compressor pump 72. Valve 60, the outflow actuator "R-valve", controls the flow through patient outflow return line 68 (one of two discharge fluid conduits), which ordinarily carries the bulk of the waste fluid from the body cavity. Valve 62, the shaver/suction instrument actuator "T-valve", controls the flow in the shaver suction line 69 (the second of the two fluid discharge conduits), which is usually used during shaving and burring operations during the arthroscopy. The R and T valves may be connected with a Y-tee (as shown in FIGS. 1 and 2 downstream of the body cavity) to a single vacuum line that leads to a waste receptacle, such as canister 73 in FIG. 1, a two part waste receptacle manufactured by Baxter Healthcare, part nos. 64-B38B and 23-2307C. Additional vacuum conduits and receptacles may be provided as need be, such as floor vacuum pickup 74, or a drape suction line at the patient. An optional fluid sensor such as liquid sensor 75 may be connected in-line to one or more of the lines, to indicate to the processor that liquid is still flowing through the line and exiting the body cavity 52.

Vacuum pump 72 periodically keeps vacuum tank 70 at a certain predetermined vacuum pressure, which is typically greater than the siphon effect created by atmosphere acting alone. In this way a vacuum may be formed that is independent of gravitational effects and does not depend on syphoning. Thus the vacuum fluid discharge system of the AC2000 more readily sucks out debris and waste fluid from the body cavity. A plurality of suitably placed check valves maintain the fluid discharge conduits in vacuum and prevent backflow. A filter 78 may be employed for the exhaust of vacuum compressor pump 72 to prevent contamination by any airborne waste debris. The plurality of waste receptacle canisters such as 73 and 80 are preferably disposable. The waste receptacles 73, 80 are attached to the housing for a portable, self-contained design.

Software driven processor 10 communicates with and controls all the major components of the AC2000 through I/O lines and interface and control circuitry, known per se in the art. All major components of the system communicate with the processor, which preferably is a microprocessor ($\mu$P). Thus both the peristaltic pump motor 40 and vacuum pump 72 communicate with the processor 10 through control lines. Numerous other components of the system also communicate with the processor via suitable control lines, such as the fluid interrupt sensor 15 in flow interrupt manifold 35, spiker assemblies 30, cavity pressure sensing system 56, pressure transducer 56', R-valve and T-valves 60, 62, a blood pressure monitor, fixed console 12, hand held remote console 14, water level sensors in fluid cartridge accumulator 46, and optional flow sensors 75.

To avoid potential overpressure of the supply conduit 48, an optional bypass valve may be present in the fluid supply conduit upstream of the body cavity and may act as a safety valve in the event of overpressure and/or notify the processor in the event of overpressure.

Furthermore, to aid in diagnostic procedures, there may be provided bypass ports just upstream and just downstream of the body cavity 52, on the supply and discharge lines, to allow fluid to bypass the body cavity when the two supply and discharge lines are connected through the bypass ports.

In addition, during certain procedures involving the shaving and burring of human tissue, the T-valve 62 of the waste discharge vacuum conduit 69 is "burped" or randomly or selectively opened and closed automatically from a closed state to a wide open state for a predetermined short period of time by the processor in order to help prevent the accumulation of waste debris in the shaver suction line. The R-valve 60 of the vacuum discharge conduit 68 may also be "burped" by the processor. Typically "burping" occurs every 15 seconds and upon any overpressure situation (e.g. where the cavity pressure exceeds a set pressure). Burping may also be used to reduce body cavity pressure in the event an overpressure is detected.

A fixed console 12 is used as the main display and control panel to input data into the processor and receive information relating to the status of the system, such as pressure readings, type of medical operation to be performed (e.g., lavage, drain, burr, clear view), system operations (e.g., priming the pump, pause, run, autopressure, increasing cavity pressure and/or flow rates). A portable hand held remote console is also provided with some of the same features as the fixed console for use by the surgeon performing the arthroscopy.

Though the preferred embodiment of the invention is for use in performing arthroscopic surgery with saline fluid, other fluids may be employed in the present invention to perform other surgical operations, without departing from the scope of the present invention.

Turning attention to FIGS. 2 and 3 regarding the overall operation of achieving an uninterrupted supply of saline irrigation fluid, there is shown a perspective view of the AC2000 in one preferred embodiment of the fluid management system a housing 15, with a cabinet, having a four shelf trays 90, each of which has three bays, which are concave, inclined at an angle to the horizontal, and receive saline bags 20. The bags are made of the flexible plastic material, with a outflow port nozzle 95 that receives the saline bag spiker, as shown in FIG. 3b. While in a preferred embodiment the bags are flexible and hold 3000 ml of saline fluid, other size bags and different types of containers, including rigid containers, may be employed.

The housing 15 of the AC2000 is mounted on wheels or coasters with a plurality of handles for maximum mobility and a swinging door (not shown) covering the front. The unit is portable, and stands 60" inches high and weighs approximately 180 lbs. when fully loaded. Console 12 gives the user information and perform vital functions as described further herein.

Optionally disposable, but reusable, flexible tubing 22 leads from the spiker assembly 30 of the saline bags to the fluid interrupt sensing manifold 35. The spiker assembly, as described further herein, is constructed so flexible tubing 22 remains closed to atmosphere, and the spiker needle trocar is ordinarily withdrawn into a spiker housing assembly when not inserted into a saline bag, thus preventing saline fluid from leaking and atmosphere from being introduced.

Two sets of tubing are found on the AC2000, an outer set and inner set. The outer set is designed to be detachable from the AC2000 and ordinarily be disposable (the preferred U.S. practice) but may be sterilized and reused. The outer tubing set comprises the patient inflow line 48, the pressure sense line 54, a pressure compensating line for the pressure transducer, as shown in FIG. 7 and as further described herein, at least one patient outflow line, such as line 68 (as best seen in FIG. 1), which is connected to vacuum, an optional second vacuum outflow line for a shaver or other vacuum related instrument, such as line 69, a floor waste retrieval line 74 (as seen in FIG. 2), a drape fluid retrieval line (not shown) and other optional lines leading to the patient. These lines are bundled for convenience as one would commonly do in electrical wiring for convenient handling. One advantage of providing for shaver flow requirements with the AC2000 tubing set is the reduction of tubing packages required for surgeries.

The inner tube set, which may also be disposable (as per U.S. medical practice) but can be reused, consists of the tubing leading from the saline bags to the spiker device, the tubing 22 interconnecting adjacent spikers and leading to the manifold 35, the inflow line 42 leading from the manifold 35 to the peristaltic pump and around the head to the cartridge accumulator 46.

Because of the different tubing sizes available for different bundles, each packaged tube set may be equipped with an identifying means such as a barcode or a magnetic strip which communicates to the AC2000 processor the particular type of procedure for which the packaged tubeset is intended to be used. Once the particular type of procedure is known to the AC2000, it may then automatically initialize its various subsystems to accommodate the particular procedure identified. The tube set contain additional tubing beyond the tubing contained in conventional arthroscopic or fluid related systems.

Turning attention now to FIG. 3, there is shown the spiker assembly of the AC2000. FIG. 3*a* shows a top view of a shelf with the left hand side cut away to expose the piston cylinder 140 that drives the spiker 30, the middle view is of the slots 31 in the shelf that hold the spiker assembly, which is snap fit in, while the right hand side of FIG. 3*a* shows a top view of a spiker assembly 30 engaging a saline bag 20. As shown in FIG. 3*b*–3*f*, a retractable and protractile hollow piston 110 has a plunger 115 with at its tip a trocar or hollow needle spiker 120, and is housed in a slidable but fluid tight manner in the cylindrical housing chamber 124. O-rings 117, 122 provide a fluid tight seal between the hollow piston and the outside, so that air and contaminants are not introduced into the system during the changing of the saline bag when the piston is retracted and during operation when the piston is protracted.

The housing chamber 124 is detachably fixed at its base to the cabinet in a snap-fit manner, as can be seen by examining FIGS. 3*b* and 3*c* in reference to the slots 31 in FIG. 3*a*. A safety arming switch (not shown) may be triggered to notify the processor when the spiker assembly is in place so that the driving pneumatic cylinder 140 of the piston plunger 115 of piston 110 may be armed to fire. The housing chamber 124 has fluid ports 126 on each side of it, which when aligned with corresponding ports 128 on the piston plunger 115 allow fluid communication with the spiker bag contents and the AC2000, and allow the automatic spiker stations (the spikers at each bag) to communicate with one another and downstream with the manifold 35 via shelf conduit tubing 22 which interconnects serially the spiker stations.

As shown in FIGS. 3*b*–3*d*, actuation of the trocar spiker is through a linear actuator such as a pneumatic cylinder 140 which receives at its rod end 150 the vertical projection 152 that is fixed to the piston plunger 115, and fits through a slot in the shelf of the housing. When the pneumatic cylinder is actuated in response to a signal from the processor the piston retracts and moves the plunger 115 forward through its housing 124 and extends the trocar tip 120 past the housing tip portion 160, which is engaged with the saline bag tubing, causing the trocar tip to pierce the sterile membrane of the saline bag. A safety latch (not shown) may be set to act as a stop to keep the pneumatic cylinder from retracting, and the safety may be disarmed by the processor to arm the spiker. Fluid begins to flow through the trocar and the hollow piston plunger, then through the side ports and into the cabinet supply conduits.

Although in a preferred embodiment the saline bags are spiked sequentially by the AC2000. As can be seen by inspection the sequential firing should be done in an orderly manner from left to right starting with spiking the bag furthest from the manifold 35 so that the closure of one spiker station to flow when a saline bag is exhausted does not block the other adjacent bags. Though in a preferred embodiment the spiking of saline bags is sequential, it is within the scope of the present invention that two or more bags may be simultaneously spiked if so desired, in a similar orderly manner.

Turning attention now to FIG. 4, there is shown the flow interrupt safety manifold used in the fluid management system. The manifold 35 allows fluid communication between each shelf level of the supply cabinet, to allow them serial access between spiker stations on each shelf and parallel access between shelves. Thus intake ports 23 of hollow cylindrical manifold 35 each receive a portion of shelf tubing 22 from each shelf (four in the preferred embodiment shown in FIGS. 1 and 2), while outflow port 41 feeds into the supply tubing 42 that leads to the pump 40. Manifold 35 acts as a tiny reservoir of irrigation fluid, holding about 25–30 ml of fluid. When manifold 35 runs dry, it signals to the processor that the saline bag(s) feeding into the manifold has been spent (or flow has been interrupted) and another bag(s) needs to be spiked. The signal indicating that the manifold is dry is generated by flow interrupt/ air sensing fluid sensor 51, that communicates with the interior of manifold 35 through a port in the manifold that snaps into the sensor. The sensor 52 has two prongs 53 and 55, which, when submerged in fluid, conduct electricity and remain a closed circuit, but when they are exposed to air, become an open circuit. A signal indicating an open circuit is then generated and related to the processor.

As an alternative to or in conjunction with the sensor in the flow interrupt manifold 35, other means of indicating when the saline bags have run out of fluid, such as counting the revolutions of the peristaltic pump 40 and estimating the fluid displaced, or employing additional sensors, may be used in the present invention.

Turning attention now to FIGS. 5*a–c*, there is shown the removable cartridge accumulator 46 of the AC2000. As best shown in FIG. 5*a*, the cartridge receives the part of the patient inflow supply line 42 at its top end 172 that proceeds to wrap around the peristaltic pump 40, and returns to empty into the port 174 of the cartridge 46 and into the reservoir 176 of the cartridge to form a fluid reservoir having a fluid level 178. Thereupon any bubbles present settle or escape out of the saline solution, the pressure surge from the peristaltic pump is attenuated, and a reservoir of saline fluid is formed between two minimum and maximum fluid levels. As shown sterile saline irrigation fluid exits the accumulator into supply line 48. The minimum and maximum fluid levels permitted are demarcated by two fluid level sensors 182, 184, that sense the maximum and minimum fluid levels. The sensors are of the same two prong open circuit/ close circuit type as found in the flow interrupt manifold 35, where two prongs, when submerged in fluid (when fluid level 178 covers them), conduct electricity and remain a closed circuit (indicating fluid is present between the prongs), but when the prongs are exposed to air, become an open circuit. In this way the processor knows when the reservoir is nearing its capacity or when the reservoir is running dry. By receiving signals from these sensors the processor can tell whether the fluid level has reached the minimum or maximum recommended levels.

As shown in FIGS. 5*b* and 5*c*, at the back of the cartridge accumulator and inside the cartridge accumulator (making the entire unit optionally disposable) are received portions of two flexible tubes from the suction lines 68 and 69 of the patient outflow line and the shaver suction line, respectively. Compactness is achieved in the cartridge accumulator by having the two tube portions pass through into the cartridge accumulator and be joined at a Y-connection as shown, to drain via vacuum line 73' to waste canister 73. The vacuum discharge conduits 68, 69 are pinched by the R-valve and T-valve pinch valve actuators 60, 62 acting through windows 210 and 212 in the cartridge accumulator, to close the flow through the flexible tubes. In this way the R-valves and T-valves close the vacuum discharge conduits in the preferred embodiment, when it is desired to restrict the flow and/or change the pressure in the body cavity. The R-valve and T-valve actuators may be a ON/OFF type pinch actuator that either fully pinch close or are fully open, or the actuators may be variably opening and closing actuators to allow partial and variable flow through the suction line R and T valves when the valves are actuated. Suitable signals would be present from both valves to and from the processor to indicate their state and to regulate them. Processor controlled pinch valves may also be employed on the inflow line 42 or any other conduit. Other valve assemblies may be employed to restrict inflow or outflow without departing from the scope of the present invention.

The air in pressurized fluid accumulator 46 is vented to atmosphere through filtered vent port valves 220, shown in FIG. 5b.

Turning attention now to FIG. 6, there is shown the front console used in a preferred embodiment of AC2000 fluid management system. The console 12 employs a touch membrane pad for input and a LED diodes for visual display. A plurality of status lights 300 are shown on the left hand side of the console, one for each spiker station bag, to indicate which saline bags have been spiked, as the bags are spiked sequentially in the preferred embodiment. A plurality of buttons are used to communicate to the processor which operation or function is to be performed. There are buttons 302 and 304 for increasing or decreasing target flow rate and cavity pressure manually to a certain predetermined baseline level, which the processor will then automatically attempt to maintain. Other buttons provide for certain common predetermined surgical procedures such as "drain"311, "lavage" 312, "clear view" 313, "burr" and "shaver" 314 (upper and lower half of button 314). A more detailed description of these features is provided herein. In addition, an automatic pressure tracking button 319 is provided for the feature where the processor of the AC2000 will vary the pressure and flow rate into the body cavity to track the mean blood pressure of the patient, which typically varies generally periodically, as measured from a blood pressure monitor input transducer (not shown) that inputs data into the processor 10.

Further input button functions are provided on the touch pad for priming the pump to relieve the system of air and initialize it at "prime" button 316, a "pause" button 317 (lower half of button) for suspending and maintaining present system parameters, a "run" button 317 (upper half) for resuming flow.

Other buttons such as buttons 360 may be employed for arming the spiker assembly, for providing a "menu" button 320 for step by step instructions for set up and operation (which may be displayed in the LED interactive display 330), a demo or tutorial button for simulated procedures, an alarm silence button 340 for silencing any alarm speakers, a scroll button 341 scrolling through the interactive display 330, a backlight button 342 for lighting in the AC2000, such as in the spiker cabinet, a power button for powering the AC2000 and other suitable buttons for other features of the apparatus as taught herein.

Status lights are also present in console 12 for indicating various states of the AC2000. A body cavity pressure gauge with a bar graph output 375 indicates actual and/or desired cavity pressure in any preselected units, such as ft. of water or mm-Hg (with a typical range for pressure and vacuum inside the body cavity of between 0–150 mm-Hg). Display windows 370 shows selected pressure baseline settings, while windows 380 show actual pressures by the pressure sensing system of the present invention. Other status lights can indicate whether there is an overpressure (such as when the waste canisters are full or the tubing is kinked); whether flow rate is set for "max.", "high", "mid" or "low" flow rates (typically the set flow range for the AC2000 is between 0–2000 ml/min); whether bags need to be reloaded; which auto spiker station (bag) is being spiked and drained, whether there is a blockage, out of fluid, overpressure or other malfunction, and other functions of interest. The LED display 330 may output text for the operator of the apparatus. A printer port may be provided for printing data. Alarms and other audiovisual displays may be provided for certain procedures and states of the AC2000.

Turning attention now to FIG. 7, there is shown the improved cavity pressure sensing system 56 of the present invention. The AC2000 device effectively senses pressure in the surgical cavity using a differential pressure transducer and novel fluid circuits. Pressure is sensed in the surgical cavity 52 through a small diameter needle in-line with sense line 54 (e.g. an 18 gauge needle). A small diameter (e.g., approx. 0.050 inch I.D.) pressure sense line 54 and compensating line 720 (transducer vent drip line) are liquid-filled to eliminate pressure reading errors. Both the pressure sense line and the transducer vent line have air-filled portions connected to the transducer above liquid/air interface 710 (at line portions 715). The liquid/air interface 710 may be in the form of a spiral coil tubing set in the horizontal plane at 710 (perpendicular to the plane of the paper) that spirals about a vertical line parallel to line portion 715. Both lines 54, 710 are sufficient in length and configuration to assure that the liquid/air interfaces are at the same elevation to eliminate pressure reading errors. Fluid in the pressure sensing system comes from the irrigation fluid under pressure from the supply line 48 through the flow restrictors R1 and R2, and fluid in sense line 54, which connects to the surgical cavity. A compensating drip line 720 ordinarily bleeds slightly to ensure no air bubbles are trapped in the sense line 54 and parallels the sense line.

When pressure is sensed in body cavity 52, the pressure is transmitted by the fluid through the sense line 54 through a filter (not shown) to the pressure transducer 740 located on the machine housing 15. A differential pressure transducer 740 is used to measure the pressure of liquid in a cavity. A standard off the shelf A/D pressure transducer may be employed for the differential pressure transducer 740, such as sold by Motorola, part no. MPX-700DP. The head change due to any relative change of height of the sense spinal needle to the transducer is compensated by the second line on a reference pressure side of the pressure transducer, drip line 720, as can be seen in FIG. 7. This line, the drip (or compensating) line 720 further may bleed out any air trapped by dripping out a minute quantity of fluid. The "sense" line 54 and "compensating" drip line 720 are preferably of the same length, and both physically attached near the cavity. Fluid under pressure that feeds the body cavity, sense line and drip line comes from the supply pressure line 48. The fluid from this source passes through restrictors R1 and R2, which restrict the fluid flow to a very low level for accurate pressure measurement. In this manner, the two sense lines are maintained full of the sterile fluid (purged of air) to provide an accurate transmittal of pressure from the patient cavity and to compensate for fluid head differences within the pressure sense system, between the cavity and the AC2000 transducer.

The compensating line is attached to the sense line to measure the head loss or gain in the compensating line. Since the head loss or gain in both the sense line and the compensating line are identical and are physically subtracted by the differential pressure transducer, the transducer's electrical output will be a measure of only the pressure within the cavity, regardless of the difference in liquid head height between the cavity and the remote transducer.

The equation for the electrical output of the transducer is as follows:

$Pc+(P2-Pa)=P1$ and $P1-P2=Pc-Pa$, since $Pa$=atmospheric=0, then $Pc=P1-P2$

Since the transducer has some gain (K), then its electrical output is proportional to:

Volts out=$K(P1-P2)$=proportional to cavity pressure, Pc.

As explained herein, the output of the transducer 740 is supplied to a control system governed by processor 10 to regulate and control the pressure and liquid flow to the body cavity 52.

Another advantage of such a cavity sensing system, in addition to the head compensating feature, is that positive liquid flow may be maintained into the cavity during pressure sensing, which precludes the entrance of gas (or air) that could modify apparent liquid bulk modulus or provide bubbles that might cause two-state flow, water hammer or slugging in the control system.

Some additional advantages of the pressure sensing system of the AC2000 are: (a) the insertion of the slender pressure sensor (spinal needle) into the cavity does not necessarily require an incision and thus does not leave a scar; and (b) that, because of their configuration, the pressure sense lines are smaller and less cumbersome, and therefore easier for a physician to handle compared to that of conventional pressure sensing lines.

In another modification of the pressure sensing system, the compensating line may be eliminated while the overall fluid circuit remains the same. The head loss or gain that is present in the sense line may be zeroed out by the computer through software that estimates the head loss or gain and allows for that factor when computing pressure.

Turning attention now to FIG. 8, though in a preferred embodiment of the present invention, as shown in FIG. 2, the saline containers are flexible bags that are supported in bays of shelf trays of a cabinet housing, it is envisioned that a traditional upright configuration may be employed, so that the one or more flexible bags may be vertically hung from a rack in a carousel manner. This embodiment is shown in FIG. 8. In FIG. 8 the post 818 fits in a telescoping manner over post 817, allowing the carousel rack 819 to rotate, and allowing the ends of bags 810 to touch the spikers 830, which are otherwise the same as the spikers 30 shown in the other embodiments. Thus the bags 810 may still be spiked by spikers 830 in this configuration (with the spikers pointing upwards) and the irrigation fluid from the bags may then be pressurized by the system using a positive displacement pump as before; or, in the alternative, the pressurized system may be dispensed with and traditional gravity feed techniques may be employed with the spikers. Bags may be separated from one another by dividers 821 as shown. Furthermore, while a plurality of flexible bags are shown in the FIG. 8 embodiment, they may be replaced with one or more rigid and/or larger containers.

The advantage with the embodiment of FIG. 8 is that certain hospital personnel are more comfortable dealing with saline bags mounted in the traditional upright manner. Further the FIG. 8 embodiment is more portable and weighs less, about 60 lbs., than the AC2000 of FIG. 2. The display console (not shown) and other major components may be similar to the embodiment described and shown in the FIG. 2 embodiment.

Turning attention now to the embodiment of FIG. 9, there is shown another fluid management system of the present invention, which is processor based and otherwise operates the same as the FIG. 2 embodiment. A plurality of fluid bags 920, which may be larger than the average saline bag of the FIG. 2 embodiment, have their contents pumped by peristaltic pump 940 into a 3 liter accumulator reservoir 946, suspended above the patient on a IV pole 947, which has a weight sensor 947' built into it so that when the weight of fluid in the accumulator 946 drops below a certain predetermined threshold, the processor knows that the saline fluid bags need to be replenished. The accumulator 946 is pressurized and vents to atmosphere through a filtered vent 949. As before, a supply conduit 948 feeds from the accumulator into the patient. In another embodiment of the invention of FIG. 9, the accumulator is not pressurized. Pressure is produced through the gravity head associated with the accumulator being raised a certain height from the floor. In this embodiment the height of the accumulator, as determined by IV pole 947, and thus the pressure head, may be changed either manually or electro-mechanically, as is known per se in the IV pole art. A control panel and extension for this embodiment of accumulator is shown in FIG. 10.

Thus, turning attention to FIG. 10, there is shown a control device designated control unit 1001, that is designed to be used with the upright embodiment of FIG. 9, when the accumulator 946 is preferably not pressurized, though a pressurized accumulator could be used as well. In this configuration, a post 1003 is set to be clamped from and offset to an I.V. pole 1005, through a series of screw clamps 1006. The unit 1001 in turn is attached to an I.V. pole through clamps 1008. Patient inflow line 1021 would supply saline solution to the body cavity. The unit 1001 has a cantilevered boom arm 1010 with a weight sensor 1012 to measure the weight of a saline bag reservoir 946 that hangs from the cantilevered arm. A processor and associated circuitry would monitor the weight of the bag so that if a certain predetermined weight level dropped below a certain threshold, the processor would instruct the peristaltic pump 940 to pump fluid into the reservoir 946 through reservoir supply port 1020 and associated tubing, until such time that the weight sensor 1012 indicated a satisfactory amount of saline fluid was present in reservoir 946. At that point the pump 940 would be instructed by the processor to stop. At the initiation of pumping by the peristaltic pump 940 in response to a signal coming from weight sensor 1012, a count-down timing circuit (not shown), which may be a hardware timer or software that is driven by the processor, would begin to count down from a predetermined time. If the pump were to stop pumping before the count-down weight sensor 1012 that the saline reservoir 946 is full, the count-down timer would be reset to the predetermined time. If, however, the count-down timer were to reach zero (run out of time) while the pump was still pumping or powered on, it would indicate an anomalous condition that most likely means there is no fluid left in fluid bags 920. At this point an alarm may be sounded, a status light 1030 on the console of the unit 1001 may be lit, and the pump may be powered off. The unit 1001 may have its own power supply 1040 and a built in power switch 1045 for powering on the unit, as well as a start/stop switch 1050 for running the unit. Other status lights 1060 for indicating when there is a electrical misconnection may also be present.

Turning attention now to FIGS. 11A and 11B, there is shown another embodiment of the present invention, having an unpressurized reservoir 1101 that is suspended above the operating theater by a height "h", in a more traditional fashion. This configuration of hanging is favored by some health care professionals due to its familiarity and other factors. A cart 1105 having wheels 1107 and folding or telescoping arms 1109, which collapse to inside the cart when not in use, holds the reservoir 1101 of saline solution above the operating theater. Reservoir 1101 is not sealed from atmosphere and depends on a gravity head to supply pressure to a patient downstream of the reservoir. The gravity head of pressure "h" ft-water is produced when reservoir 1101 is raised by a height "h" above the operating table, as shown. This height is regulated through the operation of raising and lowering the reservoir 1101 so that the height "h" varies to give varying pressures, which in the preferred embodiment of FIGS. 11A and 11B is achieved through a cable and pulley arrangement powered by a winch. Cable 1112 is attached to reservoir 1101 at the top thereof and runs through pulley 1114, located at the top portion of the apparatus, to a winch 1116 which winds and unwinds the cable in response to a motor 1118 to vary the height "h" of the reservoir with respect to the patient. The height "h" may be controlled automatically, through processor based control means controlling the operation of winch 1116, by sensing cavity pressure in a patient's knee, such as with a pressure transducer as disclosed herein or with other pressure sensing means, to give the proper gravity head to achieve a given cavity pressure. In the alternative, the height "h" may also be controlled manually through an operator controlling the powering of winch 1116 through switch means, which may be remote from the apparatus 1105. Further, the control means may be activated through voice activated means controlled by software. Furthermore, the cable 1112 may have in-line fastening means 1120 to enable one to disconnect or break the cable at the fastening means to manually operate the height of the reservoir bag or otherwise disconnect the automatic regulation of the reservoir height. Control means 1130 may be housed inside the cart apparatus 1105 in a compact manner. A handle 1140 adds portability to the cart.

The following method steps illustrate in basic form how to set-up and use the tubing set of a preferred embodiment of the present invention as it relates to the processor based embodiments:

1. Place the spiker assembly(s) of the inflow line into the corresponding positions on the shelf(s).
2. Place the pump tubing through the pump head.
3. Snap the accumulator module to the housing of the AC2000, and connect the entry and exit ports with the tubing from the pump and to the patient.
4. Connect the ports leading to and from the inflow manifold with the tubing from each auto-spiker tubing set assembly being used for the case.
5. Attach suction lines to appropriate waste canisters.
6. If applicable, connect appropriate line to the floor and drape waste fluid collection device.
7. Attach the appropriate tube lines to the shaver or other suction related instrument, the outflow cannula and, if applicable, the drape's fluid collection pouch.
8. Prime—inflow line, pressure sense line and pressure compensation line.
9. Surgeon to insert 18 gauge needle (pressure sensing probe) into an unobstructed area of the joint/cavity.
10. Connect inflow line to inflow cannula and pressure sense line to 18 gauge needle.
11. Surgeon sets pressure and flowrate.
12. Press "Run/Pause" to start flowing to begin surgery.

A more detailed set-up and operation instruction manual for a preferred embodiment of the present invention of FIG. 2 (the AC2000) is attached hereto and forms a part of the present description of the invention as "Appendix A".

Turning attention now to certain particular operations using the AC2000, the general operating parameters for the system will be described for several typical procedures during arthroscopic surgery, such as the operations "lavage", "clear view", "prime", "drain", "burr", "pause/run", "flow", "auto pressure", "set pressure", and "set flow rates" shown in FIG. 6.

For instance, when the "clear view" function button 313, is depressed, the system provides a sequence of flow rates and pressures that attempt to clear the view (as seen through an illuminated endoscope) of debris, typically by raising the pressure from whatever baseline pressure has been set, to dilate blood vessels within the body cavity and stop any blood flow, and increasing the flow rates from whatever baseline flow rate has been set. Typically this procedure is set for a two minute cycle (the time of the cycle may be adjusted for more or less than this number) where flow rates are increased 20% from baseline rates and pressure is increased 20% from baseline pressure. The "clear view" button 313 may be re-pressed prior to the completion of the cycle to return the AC2000 to its prior settings. Built in safety features prevent the AC2000 from exceeding certain safety limits with respect to pressure limits. A status light on the console indicates the function has been selected.

Regarding the "burr/shaver" button 314, when this function is selected the AC2000 provides the optimal inflow and suction flow rates to better maintain distention of the body cavity (typically a knee or shoulder joint), minimize viewing turbulence and fluid consumption during burring and shaving, which are performed by specialized tools that may be attached to the second shaver suction line 69 as shown in FIG. 1. A slightly different flow rate between "burr" and "shaver" applies, with pressure and flow rates for "shaver" being slightly greater than for "burr", but the functions are otherwise identical. When this button is depressed the processor of the AC2000 knows to activate the second suction discharge conduit 69.

Regarding the "lavage" function button 312, this function increases and then decreases the pressure and flow rates for a predetermined period of time over a cycle. Typically the fluid cycle is factory set for an increase of 25% in baseline pressure and flow rates for 10 seconds followed by a decrease to 75% of baseline pressures and flow rates for 10 seconds.

Regarding the "pause"/"run" and drain functions, buttons 317 and 311 in FIG. 6, these functions are related to the general operation of the system. For instance, "pause" will halt the operation of the AC2000 for a predetermined period of time and then resuming at the previous levels of flow rate, pressure and other state parameters of the system; run will negate the "pause" button and otherwise will start an operation that is suspended; "drain" will drain the fluid from inside the body cavity by halting the flow along the inflow supply line and opening the R and/or T valves controlling the waste discharge conduits to drain fluid from the body cavity. The "drain" function lasts until such time that the operator depresses the "drain" button again, stopping the procedure.

Likewise, the "flow" and "pressure" buttons 302 and 304 may be manually selected to a particular predetermined baseline that the processor will attempt to smoothly track the system to follow (subject to any safety overrides as described herein). For example, in a preferred embodiment the flow rates (which typically can be set to range from 0–2000 ml/min) may be set to four predetermined rates, in descending order, such as "max.", "high", "mid" and "low". In a preferred embodiment of the AC2000, the "max." flow rate is 1200–2000 ml/min., the "high" flow rate is 750–1200 m/min., the "mid" flow rate is 300–750 ml/min., and the "low" flow rate is 0–300 ml/min.

Indicator lights may display which level has been selected. Pressure can also be manually set to a baseline pressure, in either feet of water or mm-Hg, with a bar graph display and visual gauge for both the actual and desired pressure values. Typically the present invention produces a range of pressures inside the body cavity 52 ranges between 10–150 (6.7 ft-wc), while the pressure inside the supply conduit 48, owing to pressure losses, is from between that pressure range found inside between the body cavity to up to 500 mm-Hg upstream of the body cavity. Likewise the range of vacuum produced inside the body cavity 52 by the vacuum fluid circuit ranges from up to 150 mm-Hg, while the vacuum produced in the discharge lines 68, 69, owing to vacuum pressure losses, is higher and from up to 150 mm-Hg in or near the body cavity to between 220–350 mm-Hg vacuum further downstream of the body cavity. However, greater or different pressure and vacuum values are possible within the body cavity and fluid conduits without departing from the scope of the invention. Differences in tolerance between desired pressure and actual pressure are preferably limited by the processor control system to about ±10 mm-Hg.

The processor of the present invention is software driven, with the software designed to anticipate likely flow rates, pressures, emergency conditions and other parameters as taught and disclosed herein to give stable output and prevent surges or unnecessary interruptions of the system. For example, in response to a line being kinked which would indicate a blockage, the AC2000 automatically suspends operation by going into the "pause" mode, and indicates that such a blockage is detected. Furthermore, the processor may be equipped with a table that will list indeterminate and unacceptable levels of pressure and flow rates, and either default to more acceptable levels and/or indicate an anomalous condition. With respect to all functions on the console the processor of the AC 2000 may employ algorithms to achieve a smooth, uniform tracking and performance to prevent unnecessary flow surges and overpressure or underpressure states. The processor is responsible for the numerous safety features that may be incorporated in the AC2000, such as responding to shut down or to place the system in a different state in response to such as indications out of flow in the supply conduit, no flow or lack of flow in the discharge conduits, overpressure or underpressure, blockage of the conduits, waste canister overflow, backflow, spiker arming, pressure and vacuum pump state, pressure accumulator and vacuum tank state, type of surgical procedure and other values that are taught or suggested by the present invention. Typically the processor samples the various major components of the AC2000 five times a second, though a different sampling rate may be chosen.

Although several preferred embodiments of this invention have been described in detail herein with reference to the accompanying drawings, it is to be understood that the invention is not limited to these precise embodiments, and that various changes and modifications may be affected therein by one skilled in the art without departing from the scope or spirit of the invention. Accordingly it is to be understood that while the invention has been described above in conjunction with preferred specific embodiments, the description and examples are intended to illustrate and not limit the scope of the invention, which is defined by the scope of the appended claims.

We claim:

1. A fluid management system for irrigation of a body cavity comprising:

a reservoir of fluid suspended a height "h" above the body cavity, said reservoir containing a fluid discharge conduit leading from said reservoir to the body cavity, with said reservoir providing fluid under pressure to said body cavity in accordance to the height "h" in gravitational head;

means for raising and lowering said reservoir of fluid to vary said gravitational head of pressurized fluid to said body cavity;

control means to control said means for raising and lowering said reservoir of fluid;

wherein said control means are processor based and further comprising means to sense pressure inside said body cavity, said control means controlling said means for raising and lowering said reservoir of fluid to vary the height "h" in response to said means to sense pressure.

2. A fluid management system for irrigation of a body cavity comprising:

a reservoir of fluid suspended a height "h" above the body cavity, said reservoir containing a fluid discharge conduit leading from said reservoir to the body cavity, with said reservoir providing fluid under pressure to said body cavity in accordance to the height "h" in gravitational head;

means for raising and lowering said reservoir of fluid to vary said gravitational head of pressurized fluid to said body cavity, wherein said means for raising and lowering said reservoir of fluid comprises a winch attached to a cable, a pulley, and an arm holding said pulley, said cable attached to said reservoir of fluid and disposed about said pulley, and a motor controlling the winding and unwinding of said winch.

3. The invention according to claim 2, wherein said means to control said means for raising and lowering control the powering on and off of said motor.

4. A portable fluid management system for irrigation of a body cavity comprising:

a cart having wheels and at least one vertically extending arm;

a pulley mounted on said arm, said pulley guiding a cable;

a reservoir of fluid attached to said cable, said reservoir having a fluid discharge conduit leading from said reservoir to withdraw fluid from said reservoir to a body cavity;

a winch driven by a motor for reeling in said cable, wherein the length of the cable determines the height said reservoir is raised above ground and the amount of gravitational head pressure supplied by said reservoir;

means to control said winch; and means to sense the pressure in said body cavity, wherein said control means in response to said pressure sensing means may drive said winch to adjust the height of said reservoir.

5. The invention according to claim 4, wherein said arm is telescoping, said control means comprises a processor that is voice activated, and further comprising fastening means on said cable to disconnect said cable from attachment to said winch.

6. The invention according to claim 4, wherein pulley is supported by two arms, said arms being telescoping, and wherein said control means, said winch and said motor are housed inside said cart.

7. In an improved fluid management system for irrigation of a body cavity comprising:

a supply of irrigation fluid;

an accumulator, mounted on a post, for receiving said irrigation fluid;

means for sensing the amount of fluid in said accumulator, said sensing means mounted on said post;

means for pumping said irrigation fluid from said irrigation fluid supply to said accumulator;

a supply conduit connecting said accumulator to a body cavity for irrigation of said body cavity;

control means for sensing said means for sensing the amount of fluid in said accumulator to control the pumping of said pumping means;

wherein said accumulator is kept full by said control means to provide a reservoir of fluid, wherein:

said control means further comprises a count-down timer set to count down time from a predetermined time, and actuated to start counting down when said pumping means are powered on to pump irrigation fluid to said accumulator in response to said sensing means;

said count-down timer reset to said predetermined time when said pumping means are powered off to stop pumping irrigation fluid in response to said sensing means;

means for producing an alarm in response to said count-down timer, wherein said count-down timer produces a signal to activate said alarm means when said count-down timer reaches zero.

8. The invention according to claim 7, further comprising:

a unit housing said alarm means and said post, said unit having a clamp for attachment to an I.V. pole;

said pumping means is a peristaltic pump;

said sensing means is a sensor to sense the weight of fluid in said reservoir, said reservoir hanging from a cantilevered arm attached to said post.

* * * * *